(12) United States Patent
Giulio

(10) Patent No.: US 9,198,979 B2
(45) Date of Patent: Dec. 1, 2015

(54) THIAZOLIDINE LINKER FOR THE CONJUGATION OF DRUGS TO ANTIBODIES

(71) Applicant: Philogen S.P.A., Sovicille (SI) (IT)

(72) Inventor: Casi Giulio, Glattpark (CH)

(73) Assignee: Philogen S.P.A., Sovicille (IT)

( * ) Notice: Subject to any disclaimer, the term of this patent is extended or adjusted under 35 U.S.C. 154(b) by 0 days.

(21) Appl. No.: 13/849,947

(22) Filed: Mar. 25, 2013

(65) Prior Publication Data

US 2013/0309257 A1    Nov. 21, 2013

Related U.S. Application Data

(63) Continuation-in-part of application No. PCT/EP2011/004664, filed on Sep. 16, 2011.

(30) Foreign Application Priority Data

Sep. 29, 2010  (EP) .................................... 10011374

(51) Int. Cl.
*A61K 47/48* (2006.01)
*A61K 49/00* (2006.01)

(52) U.S. Cl.
CPC ..... *A61K 47/48715* (2013.01); *A61K 47/48438* (2013.01); *A61K 47/48569* (2013.01); *A61K 49/0043* (2013.01); *A61K 49/0058* (2013.01)

(58) Field of Classification Search
CPC .................. A61K 47/48438; A61K 47/48569; A61K 47/48715; A61K 49/0058
USPC .............. 424/181.1, 179.1; 530/330; 548/544
See application file for complete search history.

(56) References Cited

U.S. PATENT DOCUMENTS

| | | | | |
|---|---|---|---|---|
| 4,596,768 | A * | 6/1986 | Singh et al. ..................... | 435/7.9 |
| 2006/0233794 | A1* | 10/2006 | Law et al. .................. | 424/144.1 |
| 2008/0124331 | A1* | 5/2008 | Cairns et al. ............... | 424/138.1 |

FOREIGN PATENT DOCUMENTS

| WO | WO 2004/073656 | A2 | 9/2004 |
|---|---|---|---|
| WO | WO 2009/151491 | A9 | 12/2009 |
| WO | WO 2011/017837 | A1 | 2/2011 |

OTHER PUBLICATIONS

Villa et al.; Title: A high-affinity human monoclonal antibody specific to the alternatively spliced EDA domain of fibronectin efficiently targets tumor neo-vasculature in vivo; Int. J. Cancer, 122, 2405-2413, published Jun. 1, 2008 by Wiley.*
MedKoo, Product information of Cemadotin; downloaded from http://www.medkoo.com/Anticancer-trials/Cemadotin.htm on Nov. 10, 2014.*
Bonnet, et al., "Synthesis by Chemoselective ligation and Biological evaluation of Novel Cell-Permeable PKC PKC-ZETA Pseudosubstrate Lipoppeptides", Journal of Medicinal Chemistry, vol. 44, No. 3, Feb. 1, 2001, pp. 468-471.
Lu, et al., "Issues related to targeted delivery of proteins and peptides", AAPS Journal, vol. 8, No. 3, Jul. 21, 2006, pp. E466-E478.
Trüssel, Sabrina, "New Strategy for the Extension of the Serum Half-Life of Antibody Fragments", Bioconjugate Chemistry, vol. 20, 2009, pp. 2286-2292.
Trüssel, Sabrina, "Novel strategies for the site-specific chemical modification of therapeutic antibodies—Dissertation for the degree of Doctor of Sciences", 2011, 5 pages.
Zatsepin, et al, "Synthesis of peptide-oligonucleotide conjugates with single and multiple peptides attached to 2'-aldehydes through thiazolidine, oxime, and hydrazine linkages", Bioconjugate Chemistry, vol. 13, No. 4, Jul. 2002, pp. 822-830.
Zhang, et al., "Preparation of functionally active cell-permeable peptides by single-step ligation of two peptide modules," Proceeding of the National Academy of Science USA, vol. 95, No. 16, Aug. 4, 1998, pp. 9184-9189.
International Search Report and Written Opinion—Application No. PCT/EP2011/004664, dated Jan. 3, 2012, 20 pages.

* cited by examiner

*Primary Examiner* — Johann R Richter
*Assistant Examiner* — Yanzhi Zhang
(74) *Attorney, Agent, or Firm* — Sunstein Kann Murphy & Timbers LLP

(57) ABSTRACT

In one aspect, there is provided a protein-drug conjugate compound comprising a protein covalently attached by a linker to one or more drug moieties, wherein the linker has a half-life of from 1 hour to 50 hours in phosphate buffered saline at 37° C. A carbonyl derivative of LU103793 is also described that can be used in a protein-drug conjugate compound comprising an antibody covalently attached by a linker to the drug moiety comprising, consisting or consisting essentially of the carbonyl derivative.

10 Claims, 22 Drawing Sheets
(8 of 22 Drawing Sheet(s) Filed in Color)

CEVPQLTDLSFVDITDSSIGLRWTPLNSSTIIGYRITVVAAGEGIPIFEDFVDSS
VGYYTVTGLEPGIDYDISVITLINGGESAPTTLTQQTRSHHHHHH a Preparation of S-4-(aminomethyl)benzyl ethanethioate b Syntesis of CemCH$_2$-SH m=0,1
n= 0,1,2
$R_1$= H, $CH_3$, Alkyl, Heteroatom
$R_2$= H, $CH_3$, Alkyl, Heteroatom
X= H, Alkyl, Heteroatom
Y= H, Alkyl, Heteroatom The ring might also be heterocyclic

THIAZOLIDINE LINKER FOR THE CONJUGATION OF DRUGS TO ANTIBODIES

This application is a continuation-in-part application of PCT/EP2011/004664, filed Sep. 16, 2011, which claims priority to EP 10013274.5, filed Sep. 29, 2010.

FIELD OF THE INVENTION

The present invention relates to the field of protein-drug conjugates (PDCs) for the delivery of drugs. In one embodiment, the conjugate is an antibody-drug conjugate (ADC) to target tissues or cells. In particular, the present invention relates to the application of ADCs for the delivery of drugs that can kill or inhibit tumour cells.

BACKGROUND

ADCs can be used for the local delivery of drugs that can kill or inhibit the growth or division of target tissues or cells. The use of ADCs for the local delivery of cytotoxic or cytostatic agents to kill or inhibit tumour cells in the treatment of cancer has been described (see *Anticancer Research* (1999) 19:605-614; and *Adv. Drug Delivery Rev.* (1997) 26:151-172). Theoretically, the approach allows targeted delivery of a drug moiety to tumours, and intracellular accumulation therein, where systemic administration of these unconjugated drug agents may result in unacceptable levels of toxicity to normal cells as well as the tumour cells sought to be eliminated (*Lancet* pp. (Mar. 15, 1986):603-05; and "Antibody Carriers Of Cytotoxic Agents In Cancer Therapy: A Review," (1985) in Monoclonal Antibodies '84: Biological And Clinical Applications, A. Pinchera et al. (ed. s), pp. 475-506). Maximal efficacy with minimal toxicity is therefore the ideal goal.

Early work on ADCs discovered that chemical linkages used often resulted in the loss of a drug's potency in vitro and in vivo. Thus, it was realised that a drug would ideally need to be released in its original form in order to be a useful therapeutic. Work thus concentrated on the nature of the chemical linker between the drug and the antibody. This approach was described in *Science* (1993) 261:212-215 showing that antibody-doxorubicin conjugates, prepared with linkers, could be used to treat mice bearing human tumour xenografts.

Further efforts to design and refine ADCs generally focused on the selectivity of monoclonal antibodies (mAbs), the linkers used to link the antibody to the drug and/or drug-releasing properties. Both polyclonal antibodies and monoclonal antibodies have been reported as useful in these strategies. Drugs that have been used include daunomycin, doxorubicin, methotrexate, mitomycin, neocarzinostatin and vindesine. Toxins have also been used in antibody-toxin conjugates including bacterial toxins—such as diphtheria toxin; plant toxins—such as ricin; small molecule toxins—such as geldanamycin, macrocyclic depsipeptides and calicheamicin. The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

An example of successful monoclonal antibody therapy is Herceptin® (trastuzumab), a recombinant DNA-derived humanized monoclonal antibody that selectively binds with high affinity to the extracellular domain of the human epidermal growth factor receptor 2 protein, HER2 (ErbB2) (see *Science* (1985) 230:1132-9; and *Science* (1989) 244:707-12). Although Herceptin® has been a breakthrough in treating patients with ErbB2-overexpressing breast cancers that have received extensive prior anti-cancer therapy, the majority of the patients in this population fail to respond or respond only poorly to Herceptin® treatment. Studies in tumour bearing mice have revealed that only tumour cells around the tumour neo-vasculature are targeted by the antibody in vivo.

It is now accepted that the growth of solid tumours is dependent on their capacity to acquire a blood supply, and much effort has been directed towards the development of agents (known as anti-angiogenics) that disrupt this process. More recently, it has become apparent that targeted destruction of the established tumour vasculature is another avenue for therapeutic intervention.

The present invention relates inter alia to improvements in ADCs, especially in ADCs that be used to target vascular tumours.

SUMMARY OF THE INVENTION

The present invention is based, at least in part, on the surprising finding that a linker comprising a heterocyclic 1,3-substituted five- or six-member ring—such as thiazolidine—can be used as an effective linker for the controlled release of a drug from a PDC, particularly an ADC (eg. a non-internalising ADC).

The present invention is also based, at least in part, on the surprising findings that: (i) carbonyl (eg. aldehyde) derivatives of LU103793 (also known as cematodin or cemadotin) can function as potent cytotoxins in PDCs, whilst maintaining flexibility for PDC assembly through the presence of the carbonyl moiety; and (ii) whilst the activity of LU103793 was found to be very sensitive to modifications, it has been surprisingly discovered that the introduction of a carbonyl (eg. aldehyde) moiety to the polypeptide is not detrimental to activity which provides a useful means for further modification. Moreover, we have discovered that thiol and alcohol derivatives of cemadotin possess cytotoxic activity and offer advantages in coupling to polypeptide moieties.

Thus, in a first aspect, there is provided a protein-drug conjugate compound comprising a protein attached by a linker to one or more drug moieties, wherein the linker has a half-life of 1 hour to 50 hours in phosphate buffered saline at 37° C.

Suitably, the linker comprises a heterocyclic 1,3-substituted five- or six-member rings.

Suitably, the linker comprises the following structure:

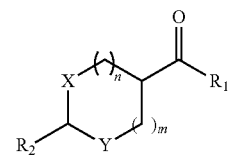

wherein X,Y are selected from group consisting of Sulphur, Nitrogen and Oxygen or a combination of two of more thereof wherein n,m can independently vary between 0 and 1; and wherein R1 and/or R2 are selected from the group consisting of a drug, a fluorophore, or a protein molecule to which the linker is attached, or a combination of two or more thereof.

Suitably, the linker is selected from the group consisting of thiazolidine, 1,3-thiazinane, oxazolidine, 1,3-oxazirane, 1,3-dioxolane, 1,3-dithiolane, 1,3-dithiane, 1,3-oxathiolane, 1,3-oxathiane, imidazolidine, hexahydropyrimidine or an analogue or derivative thereof.

Suitably, the linker comprises thiazolidine or an analogue or derivative thereof.

Suitably, the linker is modified at the benzaldehyde moiety.

The linker can be attached to a cysteine residue in the protein molecule. In one embodiment, it attached to an N-terminal cysteine.

If necessary, an N-terminal cysteine can be provided by modification of the target protein to incorporate an N-terminal cysteine residue.

In one embodiment, an N-terminal cysteine-like functionality can be provided by modification of the protein with a bifunctional ligand comprising a maleimide ring and a thiazolidine protected cysteine group. In one embodiment, the linker has the structure of the compound prepared in the scheme shown in FIG. 16a.

Optionally, one or more Glycine spacers can be incorporated into the linker.

Suitably, the drug moiety has cytotoxic and/or cytostatic and/or biocidal activity.

Suitably, the cytotoxic drug is dolastatin, preferably dolastatin-15 or an analogue or derivative thereof.

Suitably, the derivative of dolastatin-15 is LU103793.

Suitably, the LU103793 is a carbonyl derivative of LU103793, preferably an aldehyde derivative, or a thiol derivative, such as an ethanethioate or a thiophenol derivative.

Suitably, the compound localises at vascular tissue or at a vascular cell in vivo.

Suitably, the compound localises at a vascular tumour in vivo.

Suitably, the compound localises at the sub-endothelial extracellular matrix in vivo.

Suitably, the compound localises at the alternatively spliced EDA domain of fribronectin and/or the alternatively spliced EDB domain of fribronectin and/or the alternatively spliced A1 domain of tenascin-C in vivo.

Suitably, the compound does not internalise into a targeted tissue or cell in vivo.

Suitably, the protein is an antibody, preferably, a human monoclonal antibody selected from the group consisting of F8, L19 or F16.

In a further aspect, there is provided a method of making a protein-drug conjugate compound comprising the steps of: either (i) reacting a protein with a linker comprising a heterocyclic 1,3-substituted five- or six-member ring to form a protein-linker intermediate; and (ii) reacting the protein-linker intermediate from step (i) with a drug moiety to form the protein-drug conjugate; or (i) reacting a drug moiety with a linker comprising a heterocyclic 1,3-substituted five- or six-member ring to form a drug-linker intermediate; and (ii) reacting the drug-linker intermediate with a protein to form the protein-drug conjugate.

In one embodiment, the linker is formed in situ by reaction between a functional group on the protein and a functional group on the drug or label molecule. In a referred embodiment, the functional group on the protein is an N-terminal cysteine residue or a group with N-terminal cysteine-like functionality. The functional group on the drug or label is preferably an aldehyde group. In one embodiment, the functional groups are those set out in the scheme shown in FIG. 12a. The reaction produces a linker molecule in situ, which can be a thiazolidine linker.

In another embodiment, a thiol reactive group on the drug or label can be used to create a disulphide bond between a thiol group on the protein, for example provided by a cysteine residue, and the thiol group on the drug or label.

In a further embodiment, alcohol functional groups on the drug or label can be exploited to combine with ester or carbamate functional groups.

In a further aspect, there is provided the use of a heterocyclic 1,3-substituted five- or six-member ring as a linker in a protein-drug conjugate compound.

In a further aspect, there is provided a carbonyl derivative of LU103793, preferably an aldehyde derivative; a thiol derivative; and/or an alcohol derivative.

In a further aspect, there is provided a protein-drug conjugate compound comprising a protein covalently attached by a linker to one or more drug moieties, wherein said drug moiety comprises, consists or consists essentially of the carbonyl derivative of LU103793 according to the present invention.

Suitably, the linker comprises a heterocyclic 1,3-substituted five- or six-member ring.

In a further aspect, there is provided a method of making a protein-drug conjugate compound comprising the steps of: (i) preparing a carbonyl derivative of LU103793; (ii) reacting a protein with a linker to form a protein-linker intermediate; and (iii) reacting the carbonyl derivative of LU103793 from step (i) with the protein-linker intermediate from step (ii); or (i) preparing a carbonyl derivative of LU103793; (ii) reacting the carbonyl derivative of LU103793 from step (i) with a linker reagent to form a drug-linker intermediate; and (iii) reacting the drug-linker intermediate with a protein to form the protein-drug conjugate.

In a further aspect, there is provided the use of a carbonyl, thiol or alcohol derivative of LU103793 in the preparation of a protein-drug conjugate compound.

In a preferred embodiment, the carbonyl, thiol or alcohol derivatives of LU103793 can be used to create a linker in situ by reacting with a functional group on the protein.

In a further aspect, there is provided a pharmaceutical composition comprising the compound according to the present invention, or a pharmaceutically acceptable salt thereof, and a pharmaceutically acceptable diluent, carrier or excipient.

In a further aspect, there is provided a method for modulating (eg. decreasing or inhibiting) cell proliferation in vitro or in vivo comprising contacting a cell (eg. a cell in a cell culture medium) with the compound of the present invention.

In a further aspect, there is provided a method of treating a disease comprising administering to a patient a formulation of the compound, the derivative and/or the pharmaceutical composition according to the present invention.

In a further aspect, there is provided the compound, the derivative and/or the pharmaceutical composition according to the present invention for treating a disease.

Suitably, the disease is cancer—such as cancer that can be treated via the targeted destruction of the established tumour vasculature.

In a further aspect, there is provided an assay for detecting a cell comprising the steps of: (a) exposing the cell to the compound of the present invention; and (b) determining the binding of the compound to the cell.

In a further aspect, there is provided a kit comprising the compound, the derivative and/or the pharmaceutical composition according to the present invention, a container and a label or package insert on or associated with the container.

In a further aspect, there is provided a protein-drug conjugate obtained or obtainable by the methods described herein In a further aspect, there is provided a compound, method, use, derivative, pharmaceutical composition, assay or kit as substantially described herein with reference to the accompanying drawings.

FIGURES

The patent or application file contains at least one drawing executed in color. Copies of this patent with color drawing(s) will be provided by the Patent and Trademark Office upon request and payment of necessary fee.

FIG. 1 illustrates dolastatin 15 and its analogues.

FIG. 2 is an SDS-PAGE gel of BSA and BSA conjugates. Lanes 1-3: BSA-fluorescein conjugate loaded as 1:1, 1:5 and 1:10 dilutions. Lane 4: PageRuler ladder. Lanes 5-7: BSA-coumarine conjugate loaded as 1:1, 1:5 and 1:10 dilutions. Lanes 8-11: BSA reference standards: 1 mg/mL, 0.5 mg/mL, 0.25 mg/mL, and 0.125 mg/mL. A: Coomassie blue staining. B: Ethidium bromide fluorescence imaging.

FIG. 3 is a MALDI TOF/TOF spectra for (A) BSA, (B) BSA-fluorescein, (C) BSA-coumarin.

FIG. 4 is a FPLC of BSA conjugate with fluorescein by the thiazolidine linker. The co-elution of the protein (blue curve, 280 nm) with the fluorophore (red curve, 502 nm) is a clear indication of covalent conjugate between the protein and the dye. The decrease in intensity of the peak at 502 nm is used to determine the dye release from the conjugate.

FIG. 5 shows the release kinetics of BSA-Fluorescein conjugates: The experiments were performed in PBS buffer at pH 6.6 and 7.4 at 4° C., RT and 37° C. in an eppendorf tube or in a dialysis bag. $t_{1/2}$ thiazolidine: 37 h at pH 6.6 and 44 h at pH 7.4, both under dialysis conditions.

FIG. 6 shows the release kinetics of F8 IgG-fluorescein conjugate performed in PBS buffer at pH 6.6, at 37° C. $t_{1/2}$ thiazolidine: 34 h.

FIG. 7: In vitro cytotoxicity test. Cytotoxicity of cemadotin and cemadotin aldehyde (Cem-CHO) was measured on F9, HEK293 and HL60 cells.

Figure 8:
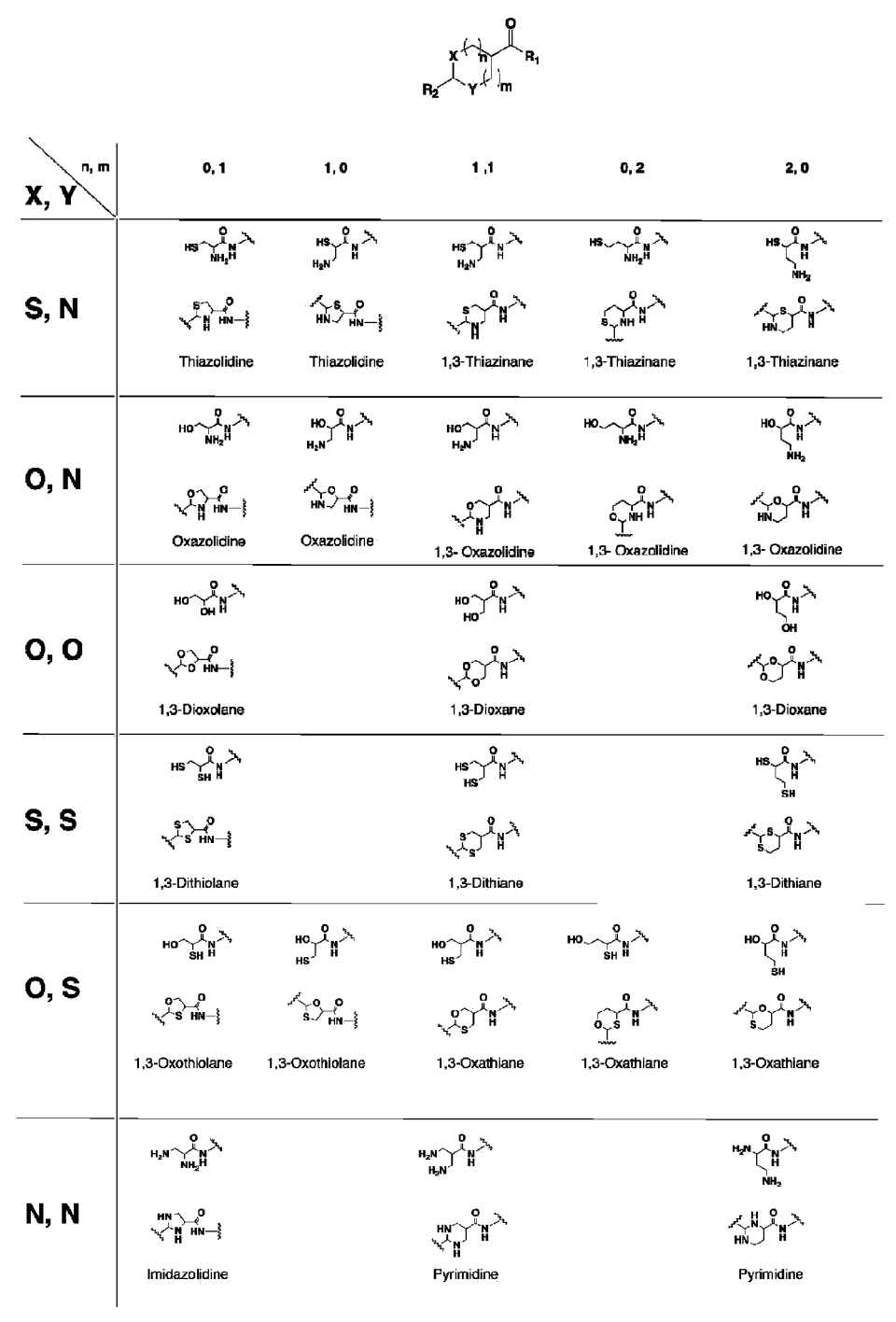

FIG. 8 illustrates various linker structures according to the present invention.

FIG. 9 illustrates the amino acid sequence of Cys-EDB, the N-terminal cysteine variant of the Extra Domain B of Fibronectin.

Figure 11:
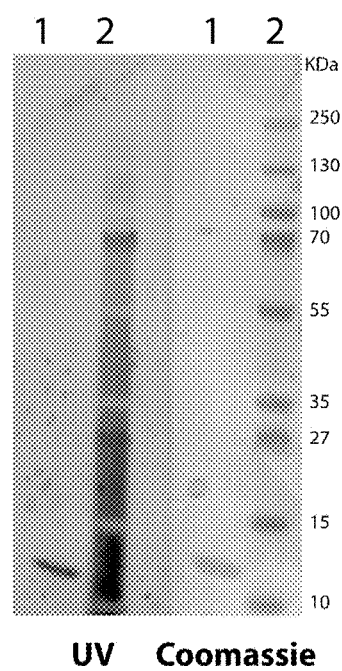

FIG. 11 shows the results of SDS gel electrophoresis using UV and Coomassie visualization. Lane 1: Fluorescein-Cys-EDB conjugate. Lane 2: Page Ruler ladder.

Figure 12:
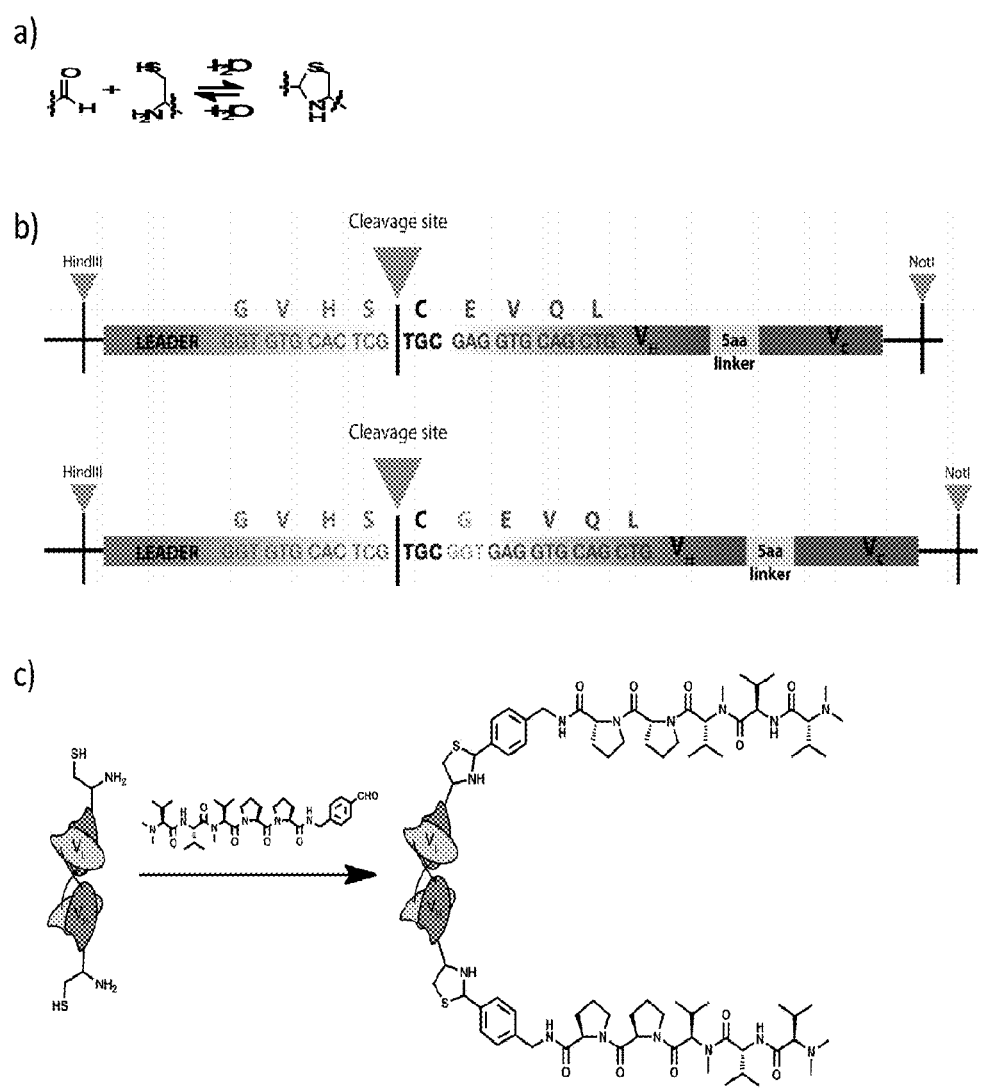

FIG. 12: a) Thiazoldine synthesis displayed as an equilibration reaction, which can be accordingly influenced. b) DNA and amino acid sequence of the newly engineered F8 mutants: the cleavage sites upon protein secretion are described for the two mutants produced (Cys and Cys-Gly). c) Schematic representation of Cys-F8 diabodies reacting with Cemadotin aldehyde to form the thiazolidine linked conjugates.

Figure 13:
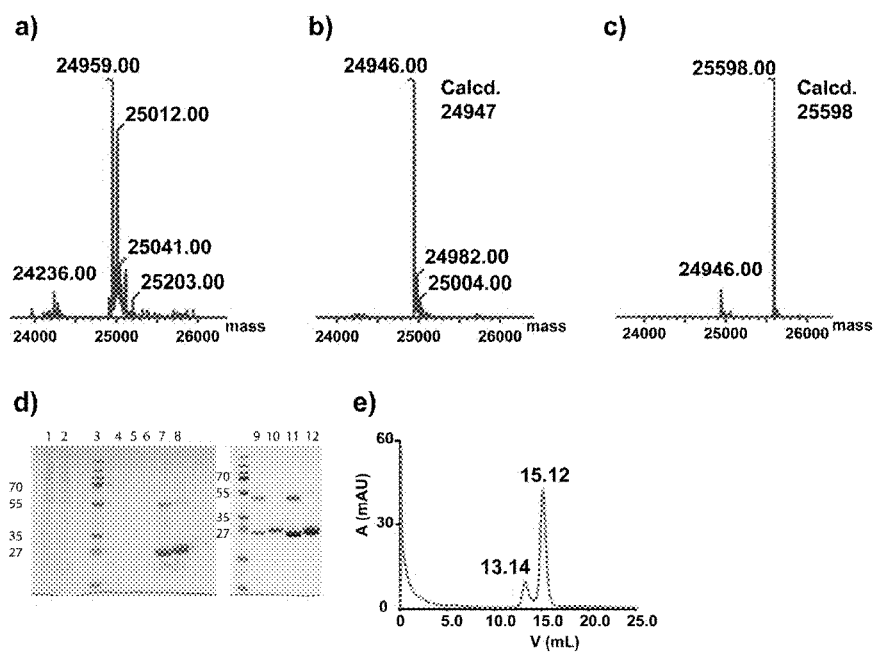

FIG. 13: a-c) ESI MS of Cys-Gly-F8 protein immediately after production, after pretreatment with DTT and MeONH$_2$ and after conjugation with Cem-CHO, respectively. d) SDS-PAGE of Cys-Gly-F8 protein production lane 1-6: input, flowthrough, PBS, PBS 0.1% tween, PBS washes. Lanes 7-8: Cys-Gly-F8 non reduced and reduced. Lanes 9-10: Cys-Gly-F8 after pretreatment non reduced and reduced. Lanes 11-12: Cys-Gly-F8 after conjugation with Cem-CHO non reduced and reduced. e) FPLC (Superdex 200 HR 10/30 column) of the purified H-Cys-Gly-F8 cemadotin conjugate.

Figure 14:
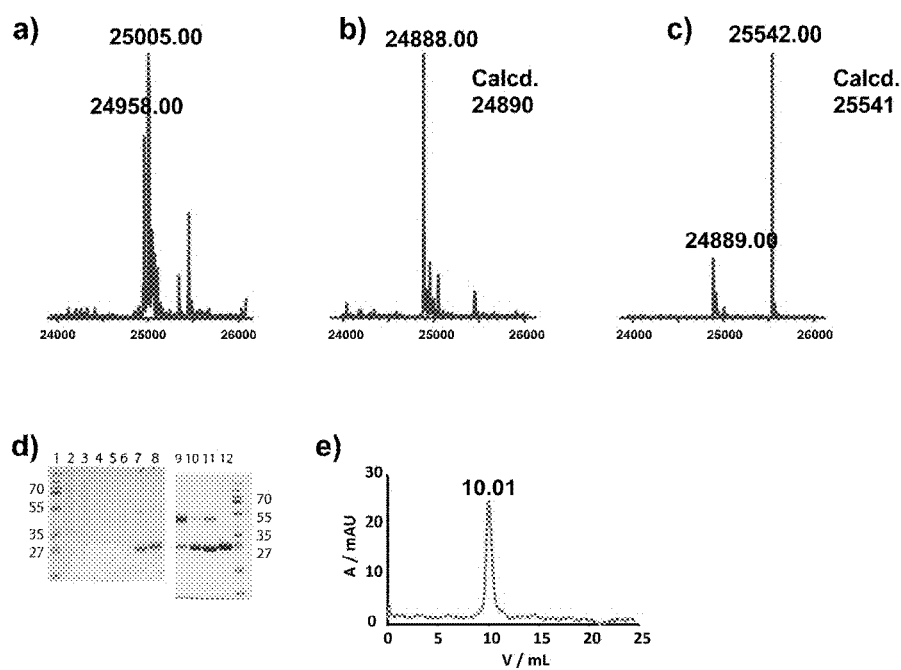

FIG. 14: a-c) ESI MS of Cys-F8 protein immediately after production, after pretreatment with DTT and MeONH$_2$ and after conjugation with Cem-CHO, respectively. d) SDS-PAGE of Cys-F8 protein production lane 1-6: input, flowthrough, PBS, PBS 0.1% tween, PBS washes. Lanes 7-8: Cys-F8 non reduced and reduced. Lanes 9-10: Cys-F8 after pretreatment non reduced and reduced. Lanes 11-12: Cys-F8 after conjugation with Cem-CHO non reduced and reduced. e) FPLC (Superdex 75 HR 10/300 GL column) of the purified H-Cys-Gly-F8 cemadotin conjugate.

Figure 15:
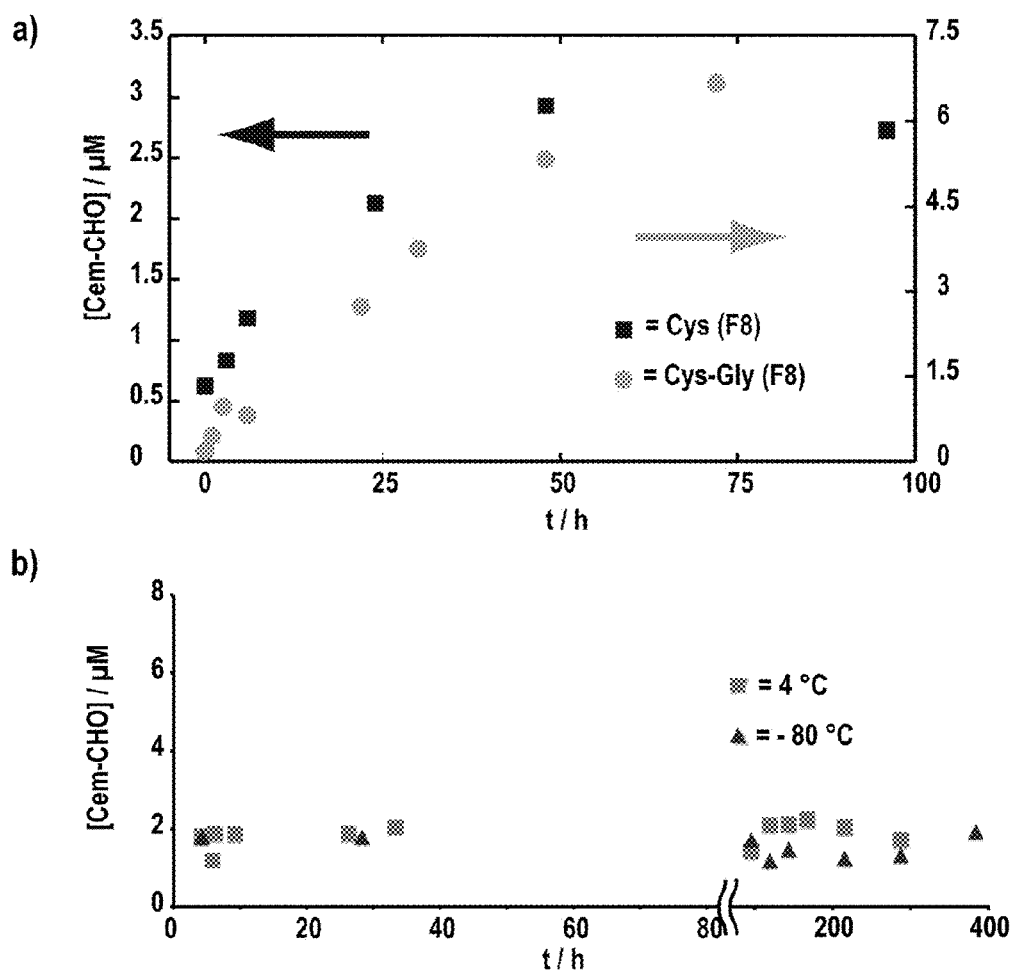

FIG. 15: a) overall release of cemadotin aldehyde from Cys (F8) and Cys-Gly (F8) conjugates; samples were collected at the time points indicated and analyzed by LC/MS/MS. b) Example of cemadotin release under storage conditions at 4° C. and −80° C. for Cys-Gly (F8) conjugate.

Figure 16:
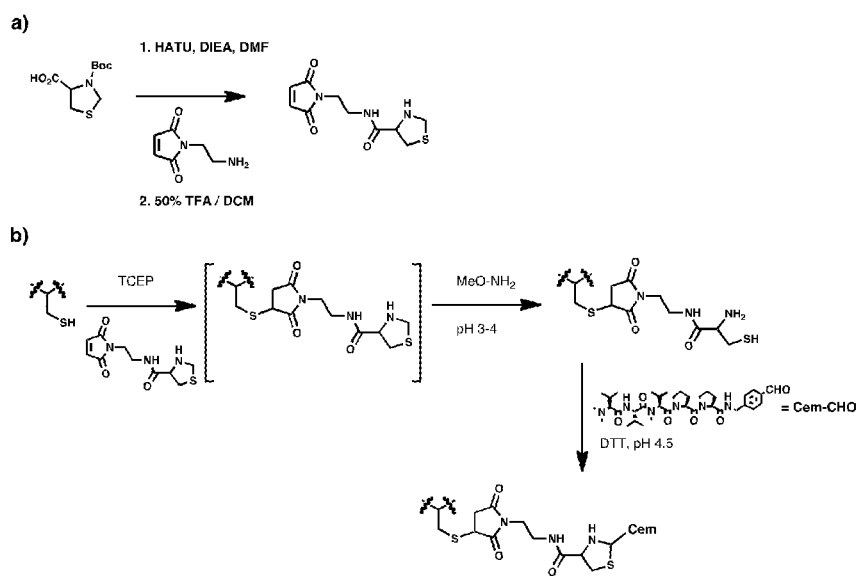

FIG. 16. a) Chemical synthesis of the bi-dentate linker. b) Chemical modification of cysteine functional groups in protein and antibodies.

Figure 17:
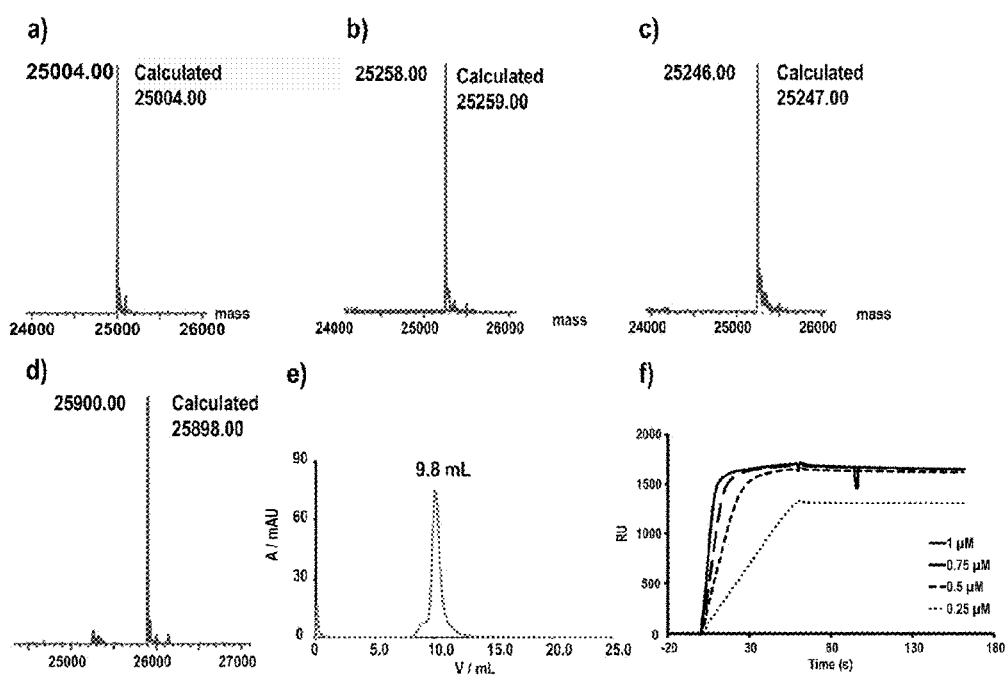

FIG. 17. a) ESI-MS of the reduced diabody F8-Cys. b-d) ESI-MS of F8-Cys antibody, after reaction with the bidentate linker, after treatment with MeONH$_2$ and after conjugation with Cem-CHO, respectively. e) FPLC (Superdex 75 HR 10/30 column) of the purified F8-Cys cemadotin conjugate. f) BIAcore analysis on a 11A12 coated chip.

Figure 18:
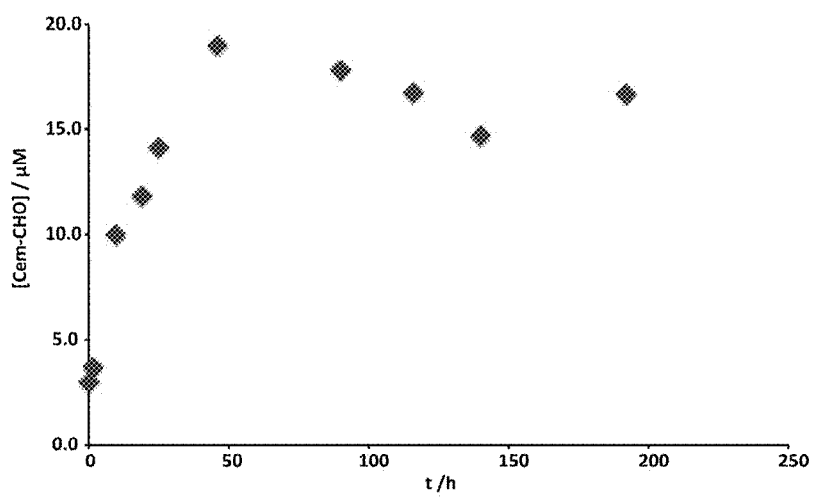

FIG. 18: overall release at 37° C. of cemadotin aldehyde; samples were collected at the time points indicated and analyzed by LC/MS/MS.

Figure 19:
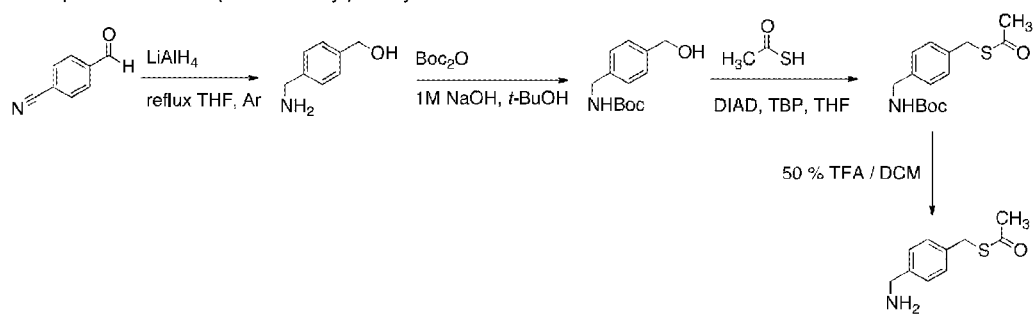
Figure 19:
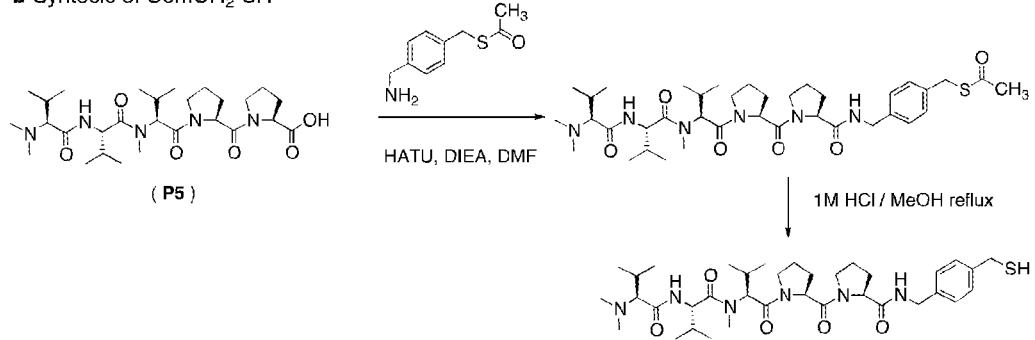

FIG. 19: Synthetic scheme for the synthesis of cemadotin analog, CemCH$_2$—SH.

Figure 20:
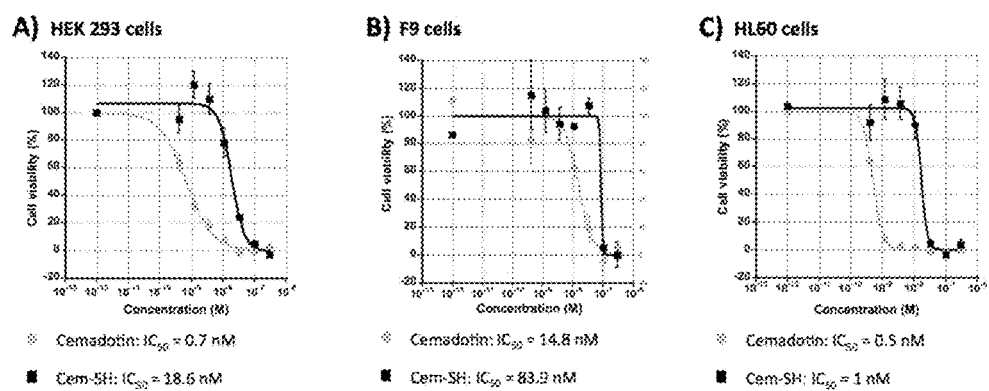

FIG. 20: Cytotoxicity assay of cemadotin and the modified derivative Cem-CH$_2$SH with different concentrations ranging from 400 pM to 300 nM. The cells were incubated at 37° C. in 5% CO2 for 72 hours and the results are presented as the average cell viability±standard deviation. The cell lines used were (A) non-tumor cell line HEK 293T, (B) tumor cell line F9 teratocarcinoma and (C) tumor cell line HL60.

Figure 21:
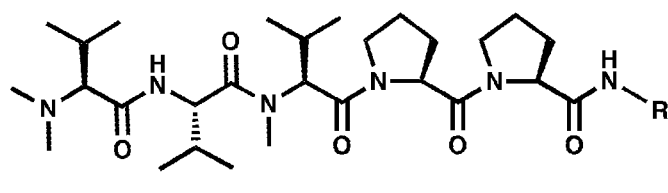
Figure 21:
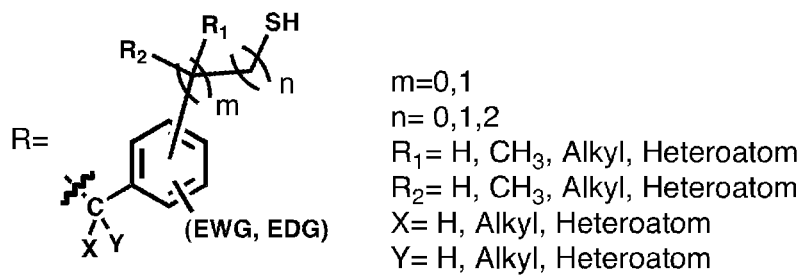

FIG. 21: General structure of possible valid alternatives to Cem-CH$_2$—SH cemadotin analogue.

Figure 22:
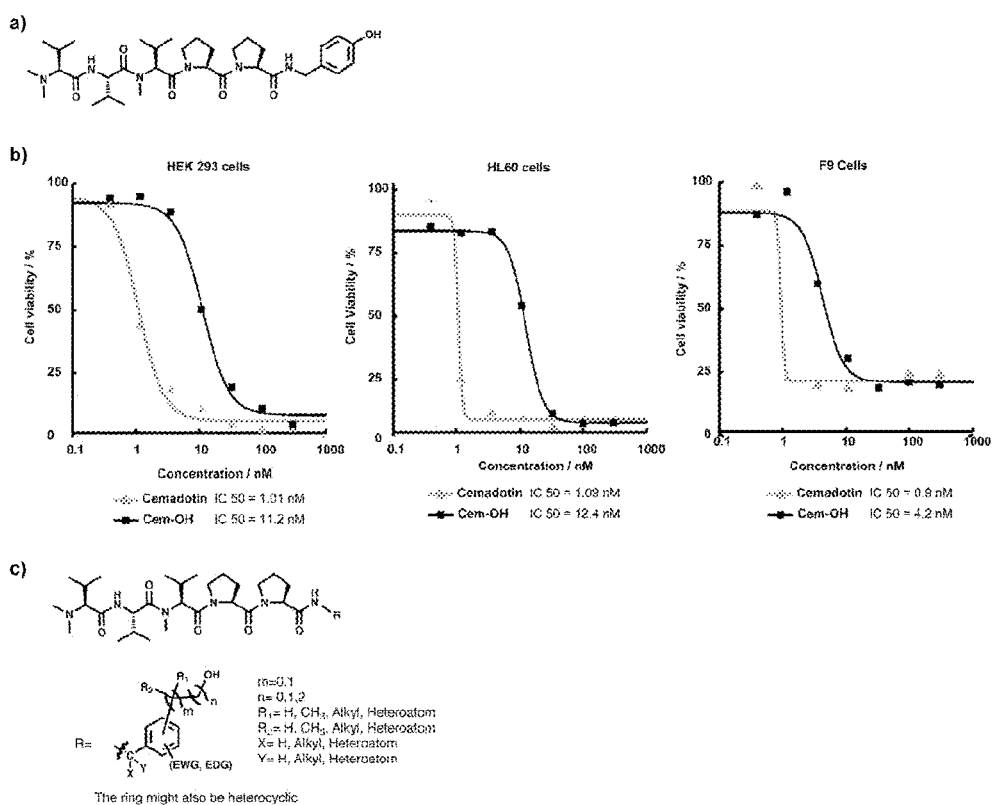

FIG. 22: a) Cem-OH. b) Cytotoxicity assay of cemadotin and the modified derivative Cem-OH with different concentrations ranging from 400 pM to 300 nM. The cells were incubated at 37° C. in 5% CO2 for 72 hours and the results are presented as the average cell viability±standard deviation. The cell lines used were respectively non-tumor cell line HEK 293T, tumor cell line HL60 and tumor cell line F9 teratocarcinoma. c) General structure of possible valid alternatives to Cem-OH cemadotin analogue

DEFINITIONS

Unless otherwise stated, all technical and scientific terms used herein have the same meanings as commonly understood by one of ordinary skill in the art to which this invention belongs. Any methods and materials similar or equivalent to those described herein can be used in the practice or testing of the present invention.

Antibody. In a particularly preferred embodiment, the protein component of the PDC is an antibody. The term "antibody" is used in its broadest sense and covers monoclonal antibodies, polyclonal antibodies, dimers, multimers, multi-specific antibodies (eg. bispecific antibodies), veneered antibodies, antibody fragments and small immune proteins (SIPs) (see Int. J. Cancer (2002) 102, 75-85). An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, ie. a molecule that contains an antigen binding site that immunospecifically binds an antigen of a target of interest or part thereof. The antibodies may be of any type—such as IgG, IgE, IgM, IgD, and IgA)—any class—such as IgG1, IgG2, IgG3, IgG4, IgA1 and IgA2- or subclass thereof. The antibody may be or may be derived from murine, human, rabbit or from other species.

Antibody fragments. The term "antibody fragment" refers to a portion of a full length antibody, generally the antigen binding or variable region thereof. Examples of antibody fragments include, but are not limited to, Fab, Fab', F(ab')$_2$, and Fv fragments; diabodies; linear antibodies; single domain antibodies, including dAbs, camelid V$_{HH}$ antibodies and the IgNAR antibodies of cartilaginous fish. Antibodies and their fragments may be replaced by binding molecules based on alternative non-immunoglobulin scaffolds, peptide aptamers, nucleic acid aptamers, structured polypeptides comprising polypeptide loops subtended on a non-peptide backbone, natural receptors or domains thereof.

Variable. This term refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity.

Antibody binding. An antibody "which binds" an antigen of interest is one that is capable of binding that antigen with sufficient affinity such that the antibody is useful in targeting a cell expressing the antigen.

Linker. A "linker" means a chemical moiety comprising a covalent bond or a chain of atoms that covalently attaches a protein to a drug moiety. The linker may be synthesised in situ. Thus, for example, a linker comprising a heterocyclic 1,3-substituted five- or six-member ring—such as thiazolidine—may be synthesised in situ by reacting a precursor—such as a N-terminal cysteine of the protein component of the PDC—with a carbonyl group—such as aldehyde—of the drug.

Half life. The term "half-life" as referred to herein in the context of a linker means the period of time taken for the covalent bond between the protein and the linker to be broken or cleaved (eg. hydrolysed) in 50% of a population of PDCs.

Derivative. A derivative includes the chemical modification of a compound. Examples of such modifications include the replacement of a hydrogen by a halo group, an alkyl group, an acyl group or an amino group and the like. The modification may increase or decrease one or more hydrogen bonding interactions, charge interactions, hydrophobic interactions, van der Waals interactions and/or dipole interactions.

Analogue. This term encompasses any enantiomers, racemates and stereoisomers, as well as all pharmaceutically acceptable salts and hydrates of such compounds.

DETAILED DESCRIPTION

Antibody

Details on antibodies, humanized antibodies, human engineered antibodies, and methods for their preparation can be found in *Antibody Engineering*, Springer, New York, N.Y., 2001.

The antibody component of the ADC includes within its scope any antibody that binds to, associates with or complexes with a receptor, antigen or other receptive moiety associated with a given target-cell population. Examples of antigens to which the antibody binds may include, lymphokines, cytokines, tumour-associated antigens, cell surface receptor proteins, cell survival regulatory factors, cell proliferation regulatory factors or molecules associated with vasculogenesis, angiogenesis and/or cell cycle regulation.

In one embodiment, the antibody component of the ADC binds to, associates with or complexes with a receptor, antigen or other moiety that is associated with vascular tissues and/or cells, suitably vascular tumour tissues and/or cells. Suitably, the antibody binds to, associates with or complexes with a receptor, antigen or other moiety associated with the alternatively spliced EDA domain of fribronectin and/or the alternatively spliced EDB domain of fribronectin and/or the alternatively spliced A1 domain of tenascin-C.

The antibody may be a polyclonal antibody ie. heterogeneous populations of antibody molecules derived from the sera of immunised animals. Various methods may be used for the production of polyclonal antibodies to an antigen-of-interest, as is well known in the art. For example, a host animal may be immunized with an antigen of interest. Adjuvants may be used to improve or increase the immunological response.

Monoclonal antibodies may also be of use in the present invention ie. an antibody obtained from a population of substantially homogeneous antibodies. Monoclonal antibodies are specific, being directed against a single antigenic site ands being directed against a single determinant on the antigen. In addition to their specificity, the monoclonal antibodies are advantageous in that they may be synthesized uncontaminated by other antibodies. Monoclonal antibodies may be prepared by the hybridoma method described in *Nature* (1975) 256:495, or they may be made by recombinant DNA methods or they may be isolated from phage antibody libraries as described in *J. Mol. Biol.* (1991), 222:581-597. Such antibodies may be of any immunoglobulin class including IgG, IgM, IgE, IgA, and IgD and any subclass thereof.

The monoclonal antibody may be a "chimeric" antibody in which a portion of the heavy and/or light chain is identical with or homologous to corresponding sequences in antibodies derived from a particular species or belonging to a particular antibody class or subclass. The remaining chain(s) is identical with or homologous to sequences in antibodies derived from another species or belonging to another antibody class or subclass, as well as fragments of such antibodies, so long as they exhibit the desired biological activity (see *PNAS* (1994) USA, 81:6851-6855).

An antibody may be a 'humanised antibody' ie. human immunoglobulins in which residues from a hypervariable region of the recipient are replaced by residues from a hypervariable region of a non-human species (see *Curr. Op. Struct. Biol.* (1992), 2:593-596). In some instances, framework region (FR) residues of the human immunoglobulin are replaced by corresponding non-human residues. Furthermore, humanized antibodies may comprise residues that are not found in the recipient antibody or in the donor antibody. The humanized antibody may comprise at least one, and typically two, variable domains, in which all or substantially all of the hypervariable loops correspond to those of a non-human immunoglobulin and all or substantially all of the FRs are those of a human immunoglobulin sequence. The humanized antibody may also comprise at least a portion of an immunoglobulin constant region (Fc).

An antibody may be a 'veneered antibody'. This refers to non-human or humanized (eg. chimeric or CDR-grafted antibodies) antibodies that have been engineered to replace certain solvent-exposed amino acid residues so as to reduce their immunogenicity or enhance their function. Veneering of a chimeric antibody may comprise identifying solvent-exposed residues in the non-human framework region of a chimeric antibody and replacing at least one of them with the corresponding surface residues from a human framework region. Veneering can be accomplished by any suitable engineering technique.

The antibody may be a bispecific antibody which may comprise a hybrid immunoglobulin heavy chain with a first binding specificity in one arm, and a hybrid immunoglobulin heavy chain-light chain pair (providing a second binding specificity) in the other arm.

The antibody may be a functionally active fragment, derivative or analogue of an antibody that immunospecifically binds to a desired antigen and which still recognises the same antigen that the antibody from which the fragment, derivative or analogue was derived. Suitable fragments of antibodies may include $F(ab')_2$ fragments (which comprise the variable region, the light chain constant region and the CH1 domain of the heavy chain) and Fab fragments, heavy chain and light chain dimers of antibodies, or any minimal fragment thereof such as Fvs or single chain antibodies (SCAs), single domain antibodies (dAbs, IgNAR, $V_{HH}$) or any other molecule with the same specificity as the antibody.

Derivatives and analogues of antibodies may include those that have been further modified by, for example, glycosylation, acetylation, pegylation, phosphorylation, amidation and/or derivatization by known protecting/blocking groups, proteolytic cleavage, linkage to a cellular antibody unit or other protein. Chemical modifications may be carried out by known techniques—such as specific chemical cleavage, acetylation and/or formylation. Additionally, the analogue or derivative may contain one or more unnatural amino acids.

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies may be commercially obtained from a wide variety of known sources. For example, a variety of antibody secreting hybridoma lines are available from the American Type Culture Collection (ATCC, Manassas, Va.). A large number of antibodies against various disease targets have been deposited at the ATCC and/or have published variable region sequences and are available for use in the present invention.

In one preferred embodiment, the antibody is a human monoclonal antibody.

In another preferred embodiment, the human monoclonal antibody is not internalised into a target cell or tissue.

In another preferred embodiment, the human monoclonal antibody is not internalised and localises in vivo at the sub-endothelial extracellular matrix of tumour blood vessels.

Some antibodies that preferred for use in the present invention include the human monoclonal antibodies F8 (specific to the alternatively spliced EDA domain of fibronectin—see *Int. J. Cancer* (2008), 122, 2405-2413; WO2008/120101); L19 (specific to the alternatively spliced EDB domain of fibronectin—see *J. Biol. Chem.* (1998) 273, 21769-21779; ATCC Patent Deposit PTA-9529); and F16 (specific to the alternatively spliced A1 domain of tenascin-C—see *Clin. Cancer Res.* (2006) 12, 3200-3208; WO2010/078916).

Vascular Targeting

It has long been known that the endothelium and surrounding stroma in tumours differs from that in normal tissue, but only recently have these differences begun to be characterized at the molecular level. Proteins that are expressed on the endothelial cells or in the surrounding stroma of tumours have been suggested for therapeutic targeting. For example, the toxin ricin was conjugated to high-affinity antibodies directed to a mouse MHC class 11 antigen in solid tumours. The conjugate was injected into mice intravenously and the antibody delivered the ricin specifically to the tumour endothelium, where it was internalized, eliciting cell death with a subsequent collapse of the vasculature and eradication of the solid tumour (see *PNAS* USA 90, 8996-9000 (1993)). Proteins expressed specifically on the tumour vasculature but not on the vasculature of normal tissues can not only be used for anti-tumour targeting but also for diagnostic (eg. imaging) purposes. The specific accumulation at the tumour vasculature actively reduces the toxic side effects that are typically associated with the anti-tumour compounds at other locations in the normal tissue and, consequently, allows for the reduction of the concentration of the toxic agents.

In one embodiment, the compound localises at vascular tissue or at a vascular cell in vivo.

In another embodiment, the compound the compound localises at the sub-endothelial extracellular matrix in vivo.

In one embodiment, the antibody component of the ADC localises at a vascular tumour in vivo. Strategies for vascular targeting in tumours have been reviewed at least in *Int. J. Cancer* (2002) 100 (2): 123-130 and *Nature Reviews. Cancer* (2005), vol. 5, 436-446. The site of vascular localisation may include, but is not limited to, the alternatively spliced EDA domain of fribronectin and/or the alternatively spliced EDB domain of fribronectin and/or the alternatively spliced A1 domain of tenascin-C.

Other sites of vascular localisation may include, but are not limited to, fribronectin, tenascin-C, ROBO4, EndoPDI, DEL1, GP34, STC1, GA733, TEM1, TEM5, TEM7, TEM8, DELTA4, Endomucin, Annexin A1, Annexin A8, Ephrin A7, Myeloperoxidase, Nucleolin, Transferrin receptor, Vitamin D binding protein, VEGF receptor 1, VEGF receptor 2, TIE2, aminopeptidase-N, endoglin (CD105), CD66, CD44, CD13, Neuropilin-1, Endoglin, HES, PSMA and ASPP1, as described in *Nature Reviews. Cancer* (2005), vol. 5, 436-446.

Other sites of vascular localisation of the ADC may include, but are not limited to fibroblast growth factor receptor-1, CD31, tumour lymphatic endothelium, and alpha V beta 3 integrin, periostin, putative G-protein coupled receptor 42, solute carrier family 2, facilitated glucose transporter member 1, versican core protein, CEACAM3, Fibromodulin, Peroxidasin homolog, probable G-protein coupled receptor 37, protein sidekick-1, alpha1A-voltage-dependent calcium channel, EMILIN2 protein, down syndrome critical region protein 8, probable G-protein coupled receptor 113, ANXA4 protein, uromodulin-like 1, m(16) scavenger receptor class F member 2, Sushi domain-containing protein 2, tumour protein, translationally controlled 1, putative G-protein coupled receptor Q8TDUO, hypothetical protein DKFZp686K0275, transmembrane protein TMEM55A, hypothetical protein Q8WYY4, family with sequence similarity 116, member A, UPF0240 protein C6orf66, cDNA FLJ45811 fis, clone NT2RP7014778, hypothetical protein DKFZp77901248, beta-ureidopropionase, hypothetical protein DKFZp434F1919, cysteine-rich with EGF-like domain protein 2, UPF0378 family protein KIAA0100, potassium voltage-gated channel subfamily H member 1.

In one embodiment, the compound does not internalise into a targeted tissue or cell in vivo.

Linker

The linker of the PDC attaches the protein to a drug moiety eg. through one or more covalent bond(s). The linker may be a bifunctional or a multifunctional moiety which can be used to link one or more drug moieties and proteins to form the PDC.

PDCs can be conveniently prepared using a linker having reactive functionality for binding to the drug moiety and to the protein. Many positions may be useful as the linkage position, depending upon the type of linkage. For example, ester linkages may be formed from a hydroxyl group on the drug moiety; ketal and hydrazone linkages may be formed from a carbonyl group on the drug moiety; amide, carbamate, and urea linkages may be formed from an amino group on the drug moiety; and various alkyl, ether, thioether, and acyl linkages may be formed from the phenyl and aryl rings on the drug moiety by Friedel-Crafts type alkylation and acylation reactions. Precursors—such as a cysteine thiol, or an amine (which may be positioned at the N-terminus and/or the C-terminus of the protein) or amino acid side chains such as lysine, of the protein can form a bond with a functional group of a linker reagent, drug moiety or drug-linker reagent. The stability of a PDC may be measured by various analytical techniques—such as mass spectroscopy, HPLC, and LC/MS.

Covalent attachment of the protein and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described in Bioconjugate Techniques (1998); Academic Press: New York, p 234-242.

The linker may be substituted with groups which modulate solubility or reactivity. For example, a substituent may increase water solubility of the reagent and facilitate the coupling reaction between the various components of the PDC.

The linker may have a reactive functional group which has a nucleophilic group that is reactive to an electrophilic group present on a protein—such as an antibody. Suitable electrophilic groups may include carbonyl groups—such as aldehyde, ketone, carboxylic acid, ester, amide, enone, acyl halide or acid anhydride. In one embodiment, the reactive functional group is aldehyde. Suitable nucleophilic groups may include hydrazide, oxime, amino, hydrazine, thiosemicarbazone, hydrazine carboxylate, and arylhydrazide. The electrophilic group may provide a convenient site for attachment to a linker.

The linker may be peptidic, comprising one or more amino acid units. Examples of amino acid linkers include a dipeptide, a tripeptide, a tetrapeptide or a pentapeptide. Amino acid linker components may be designed and optimized in their selectivity for enzymatic cleavage by a particular enzyme.

Further examples of linker reagents include, but are not limited to aldehydes—such as glutaraldehyde, N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters—such as dimethyl adipimidate HCl, active esters—such as disuccinimidyl suberate, bis-azido compounds—such as bis (p-azidobenzoyl) hexanediamine), bis-diazonium derivatives—such as bis-(p diazoniumbenzoyl)-ethylenediamine), diisocyanates—such as toluene 2,6-diisocyanate, bis-active fluorine compounds—such as 1,5-difluoro-2,4-dinitrobenzene and N-succinimidyl-4-(2-pyridylthio)pentanoate (SPP), The linker may be a dendritic type linker for covalent attachment of more than one drug moiety through a branching, multifunctional linker moiety to a protein. Dendritic linkers can be used to increase the molar ratio of drug to protein.

Several mono- and bi-dentate nucleophiles are capable of reacting with carbonyl moieties to afford heterocyclic 1,3-disubstituted five- or six-member rings. Thus, in one embodiment, the linker is a heterocyclic 1,3-disubstituted five- or six-member ring having the structure of formula I:

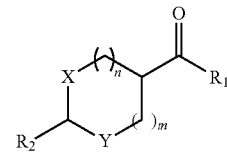

In one embodiment, X, Y are selected from group consisting of Sulphur, Nitrogen and Oxygen or a combination of two or more thereof. In another embodiment, X,Y are S,N or O,N or O,O or S,S or O,S or N,N or N,S or N,O or S,O, preferably, S,N or O,N or O,O or S,S or O,S or N,N.

In one embodiment, n, m independently vary between 0 and 1.

In one embodiment, R1 and/or R2 are selected from the group consisting of a drug, a fluorophore, or a protein molecule to which the linker is attached, or a combination of two or more thereof. In one embodiment, R1 and/or R2 is a drug (eg. LU103793), a fluorophore (eg. Fluorescein or Coumarine); or a protein molecule to which the linker is attached (eg. an antibody).

The combinations may afford a tuneable reactivity suitable for PDCs.

In the following Table are examples of possible precursors of formula I and the corresponding heterocycle:

| X | Y  | n | m | Precursor           | Heterocycle    |
|---|----|---|---|---------------------|----------------|
| S | NH | 1 | 0 | Cysteinyl           | Thiazolidine   |
| S | NH | 0 | 1 | Isocysteinyl        | Thiazolidine   |
| S | NH | 1 | 1 | β²-Cysteinyl        | 1,3-Thiazinane |
| S | NH | 2 | 0 | Homo-cysteinyl      | 1,3-Thiazinane |
| S | NH | 0 | 2 | Homo-Iso-Cysteinyl  | 1,3-Thiazinane |
| O | N  | 1 | 0 | Serinyl (Threoninyl)| Oxazolidine    |
| O | N  | 0 | 1 | Isoserinyl          | Oxazolidine    |
| O | N  | 1 | 1 | β²-Serinyl          | 1,3-Oxazirane  |

-continued

| X | Y | n | m | Precursor | Heterocycle |
|---|---|---|---|-----------|-------------|
| O | N | 2 | 0 | Homoserinyl | 1,3-Oxazirane |
| O | N | 0 | 2 | Homo-Iso-Serinyl | 1,3-Oxazirane |
| O | O | 1 | 0 | Glyceryl acid | 1,3-Dioxolane |
| O | O | 1 | 1 | 3-hydroxy-2(hydroxymethyl) propanoyl- | 1,3-Dioxane |
| O | O | 2 | 0 | Di-hydroxybutiryl- | 1,3-Dioxane |
| S | S | 1 | 0 | 1,2-dimercaptopropionyl | 1,3-dithiolane |
| S | S | 1 | 1 | 3-mercapto-2(mercaptomethyl) propanoyl | 1,3-dithiane |
| S | S | 2 | 0 | 2,4-dimercaptobutirryl | 1,3-dithiane |
| O | S | 1 | 0 | 3-hydroxy-2-mercapto-propionyl | 1,3-oxathiolane |
| O | S | 0 | 1 | 2-hydroxy-3-mercapto-propionyl acid | 1,3-oxathiolane |
| O | S | 1 | 1 | 3-hydroxy-2-(mercaptomethyl)-propanyl | 1,3-oxathiane |
| O | S | 2 | 0 | 4-hydroxy-2-mercaptobutanoyl | 1,3-oxathiane |
| O | S | 0 | 2 | 2-hydroxy-4-mercaptobutanoyl | 1,3-oxathiane |
| N | N | 1 | 0 | 2,3-diaminopropionyl | imidazolidine |
| N | N | 1 | 1 | 3-amino-2-(aminomethyl)-propionyl | hexahydropyrimidine |
| N | N | 2 | 0 | 2,4-diaminobutirryl | hexahydropyrimidine |

In a particularly preferred embodiment, the linker is a thiazolidine linker. Thiazolidine is a class of heterocyclic organic compound with a 5-membered saturated ring including a thiol and a nitrogen atom in 1, 3 arrangement and has the structure of formula II:

It is a sulphur analogue of oxazolidine. Thiazolidines may be synthesized by a condensation reaction between an amino-thiol and a carbonyl group—such as aldehyde or ketone. The reaction is reversible. Thus, according to this embodiment, there is provided a protein-drug conjugate compound comprising a protein covalently attached by a linker to one or more drug moieties, wherein the linker is thiazolidine or an analogue or derivative thereof.

In one embodiment, the linker has the structure of formula III:

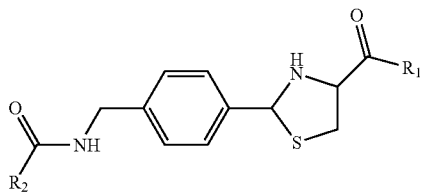

R1 and/or R2 may be a drug (eg. LU103793), a fluorophore (eg. Fluorescein or Coumarine); or a protein molecule to which the linker is attached (eg. an antibody).

Suitably, the linker is cleaved or is cleavable at the site of a tumour, for instance in the tumour vasculature.

In one embodiment, the thiozolidine linker is formed in situ as a result of the conjugation chemistry used to conjugate the drug or fluorophore to the protein molecule. The thiazolidine heterocycle can be formed by a single chemoselective reaction between an aldehyde and a 1,2-aminothiol (FIG. 12a).

In antibodies and proteins 1,2-aminothiol functions are naturally provided by N-terminal cysteines: several strategies are known to access them (Muir, T. W. Annu. Rev. Biochem 2003, 72, 249; Casi, G.; Hilvert, D. Curr. Opin. in Struct. Biol. 2003, 13, 589). However they all suffer from poor proteolytic efficiency, and troublesome purification procedures.

According to the present invention, introducing a cysteine as the first amino acid after the leader peptide in an antibody sequence provides an N-terminal cysteine containing protein upon secretion during mammalian cell production. This approach allows formation of ADCs using thiazolidine linkers by an in situ chemoselective reaction with an antibody molecule. If the antibody is a diabody format, or otherwise having two N-termini, two potential sites for addition of a drug or label can be provided.

Moreover, the present invention provides a method for site-selectively appending an N-terminal cysteine-like functional group to the C-terminus of a polypeptide. There is provided a bifunctional linker bearing a maleimide ring and a thiazolidine protected cysteine (FIG. 16a) which affords the required N-terminal-like functional group at the C-terminus of an antibody or other polypeptide.

Accordingly, in accordance with the invention, antibody molecules can be linked to cytotoxic drugs or labels using thiazolidine linkers, for example prepared in situ. The methods described allow drugs or labels to be added at any position of an antibody sequence.

In other embodiments, thiol derivatives of cytotoxic drugs can be attached to internal cysteine residues in a polypeptide by the creation of disulphide bonds.

Drug

In one embodiment, the drug is a cytotoxic agent that inhibits or prevents the function of cells and/or causes destruction of cells. Examples of cytotoxic agents include radioactive isotopes, chemotherapeutic agents, and toxins such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid and a vinca alkaloid or a combination of two or more thereof.

In one embodiment the drug is a chemotherapeutic agent selected from the group consisting of a topoisomerase inhibitor, an alkylating agent (eg. nitrogen mustards; ethylenimes; alkylsulfonates; triazenes; piperazines; and nitrosureas), an antimetabolite (eg mercaptopurine, thioguanine, 5-fluorouracil), an antibiotics (eg. anthracyclines, dactinomycin, bleomycin, adriamycin, mithramycin. dactinomycin) a mitotic disrupter (eg. plant alkaloids—such as vincristine and/or microtubule antagonists—such as paclitaxel), a DNA intercalating agent (eg carboplatin and/or cisplatin), a DNA synthesis inhibitor, a DNA-RNA transcription regulator, an enzyme inhibitor, agene regulator, a hormone response modifier, a hypoxia-selective cytotoxin (eg. tirapazamine), an epidermal growth factor inhibitor, an anti-vascular agent (eg. xanthenone 5,6-dimethylxanthenone-4-acetic acid), a radiation-activated prodrug (eg. nitroarylmethyl quaternary (NMQ) salts) or a bioreductive drug or a combination of two or more thereof.

The chemotherapeutic agent may selected from the group consisting of Erlotinib (TARCEVA®), Bortezomib (VELCADE®), Fulvestrant (FASLODEX®), Sutent (SU11248), Letrozole (FEMARA®), Imatinib mesylate (GLEEVEC®), PTK787/ZK 222584, Oxaliplatin (Eloxatin®), 5-FU (5-fluorouracil), Leucovorin, Rapamycin (Sirolimus, RAPAMUNE®), Lapatinib (GSK572016), Lonafarnib (SCH 66336), Sorafenib (BAY43-9006), and Gefitinib (IRESSA®), AG1478, AG1571 (SU 5271; Sugen) or a combination of two or more thereof.

The chemotherapeutic agent may be an alkylating agent—such as thiotepa, CYTOXAN® and/or cyclosphosphamide; an alkyl sulfonate—such as busulfan, improsulfan and/or piposulfan; an aziridine—such as benzodopa, carboquone, meturedopa and/or uredopa; ethylenimines and/or methylamelamines—such as altretamine, triethylenemelamine, triethylenephosphoramide, triethylenethiophosphoramide and/or trimethylomelamine; acetogenin—such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards—such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide and/or uracil mustard; nitrosureas—such as carmustine, chlorozotocin, fotemustine, lomustine, nimustine, and/or ranimnustine; dynemicin; bisphosphonates—such as clodronate; an esperamicin; a neocarzinostatin chromophore; aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®. doxorubicin—such as morpholino-doxorubicin, cyanomorpholino-doxorubicin, 2-pyrrolino-doxorubicin and/or deoxydoxorubicin, epirubicin, esorubicin, idarubicin, marcellomycin, mitomycins—such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites—such as methotrexate and 5-fluorouracil (5-FU); folic acid analogues—such as denopterin, methotrexate, pteropterin, trimetrexate; purine analogues—such as fludarabine, 6-mercaptopurine, thiamiprine, thioguanine; pyrimidine analogues—such as ancitabine, azacitidine, 6-azauridine, carmofur, cytarabine, dideoxyuridine, doxifluridine, enocitabine, floxuridine; androgens—such as calusterone, dromostanolone propionate, epitiostanol, mepitiostane, testolactone; anti-adrenals—such as aminoglutethimide, mitotane, trilostane; folic acid replenisher—such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; macrocyclic depsipeptides such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2''-trichlorotriethylamine; trichothecenes—such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids—such as TAXOL®. paclitaxel, abraxane, and/or TAXOTERE®, doxetaxel; chloranbucil; GEMZAR®. gemcitabine; 6-thioguanine; mercaptopurine; methotrexate; platinum analogues—such as cisplatin and carboplatin; vinblastine; platinum; etoposide; ifosfamide; mitoxantrone; vincristine; NAVELBINE®, vinorelbine; novantrone; teniposide; edatrexate; daunomycin; aminopterin; xeloda; ibandronate; topoisomerase inhibitor RFS 2000; difluoromethylomithine (DMFO); retinoids—such as retinoic acid; capecitabine; and pharmaceutically acceptable salts, acids, derivatives or combinations of two or more of any of the above.

The drug may be a tubulin disruptor including but are not limited to: taxanes—such as paclitaxel and docetaxel, vinca alkaloids, discodermolide, epothilones A and B, desoxyepothilone, cryptophycins, curacin A, combretastatin A-4-phosphate, BMS 247550, BMS 184476, BMS 188791; LEP, RPR 109881A, EPO 906, TXD 258, ZD 6126, vinflunine, LU 103793, dolastatin 10, E7010, T138067 and T900607, colchicine, phenstatin, chalcones, indanocine, T138067, oncocidin, vincristine, vinblastine, vinorelbine, vinflunine, halichondrin B, isohomohalichondrin B, ER-86526, pironetin, spongistatin 1, spiket P, cryptophycin 1, LU103793 (cematodin or cemadotin), rhizoxin, sarcodictyin, eleutherobin, laulilamide, VP-16 and D-24851 and pharmaceutically acceptable salts, acids, derivatives or combinations of two or more of any of the above.

The drug may be a DNA intercalator including but are not limited to: acridines, actinomycins, anthracyclines, benzothiopyranoindazoles, pixantrone, crisnatol, brostallicin, CI-958, doxorubicin (adriamycin), actinomycin D, daunorubicin (daunomycin), bleomycin, idarubicin, mitoxantrone, cyclophosphamide, melphalan, mitomycin C, bizelesin, etoposide, mitoxantrone, SN-38, carboplatin, cis-platin, actinomycin D, amsacrine, DACA, pyrazoloacridine, irinotecan and topotecan and pharmaceutically acceptable salts, acids, derivatives or combinations of two or more of any of the above.

The drug may be an immunotherapeutic agent.

The drug may be an angiogenesis inhibitor as described in, for example, WO2006/054908.

The drug may be an anti-hormonal agent that acts to regulate or inhibit hormone action on tumours—such as anti-estrogens and selective estrogen receptor modulators, including, but not limited to, tamoxifen, raloxifene, droloxifene, 4-hydroxytamoxifen, trioxifene, keoxifene, LY117018, onapristone, and/or fareston toremifene and pharmaceutically acceptable salts, acids, derivatives or combinations of two or more of any of the above. The drug may be an aromatase inhibitor that inhibits the enzyme aromatase, which regulates estrogen production in the adrenal glands—such as, for example, 4(5)-imidazoles, aminoglutethimide, megestrol acetate, AROMASIN®. exemestane, formestanie, fadrozole, RIVISOR®. vorozole, FEMARA®. letrozole, and ARIMIDEX® and/or anastrozole and pharmaceutically acceptable salts, acids, derivatives or combinations of two or more of any of the above.

The drug may be an anti-androgens—such as flutamide, nilutamide, bicalutamide, leuprolide, goserelin and/or troxacitabine and pharmaceutically acceptable salts, acids, derivatives or combinations of two or more of any of the above.

The drug may be a protein kinase inhibitor, a lipid kinase inhibitor or an anti-angiogenic agent.

In a preferred embodiment, the drug is a dolastatin. Dolastatins are antiproliferative agents, inhibiting the growth and reproduction of target cells and inducing apoptosis in a variety of malignant cell types. Two natural dolastatins, dolastatin 10 and dolastatin 15, have been selected for drug development based on their superior antiproliferative bioactivity. The pursuit of synthetic dolastatin analogues has led to the development of LU103793 (cematodin or cemadotin), a dolastatin 15 analogue. ILX-651 is an orally active third generation synthetic dolastatin 15 analogue. In one embodiment, the dolastatin is of the auristatin class. As used herein, the term dolastatin encompasses naturally occurring auristatins and non-naturally occurring derivatives, for example MMAE.

Figure 1:
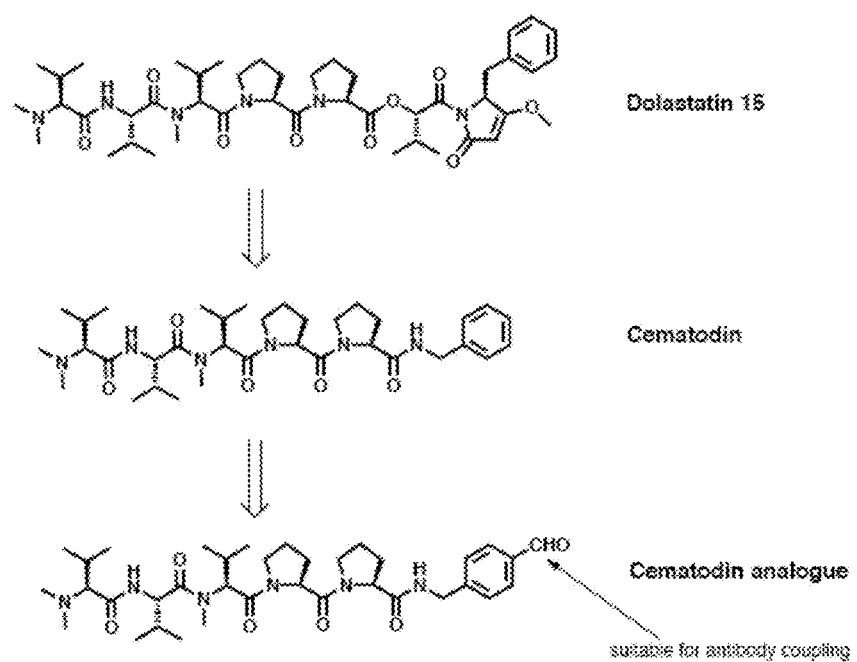

In a preferred embodiment, the drug moiety is analogue of dolastatin with a terminal carbonyl (eg. aldehyde) group, for example, at the C-terminus. In a more preferred embodiment, the drug moiety is LU103793 with a terminal carbonyl (eg. aldehyde) group, for example, at the C-terminus (see FIG. 1). Thiol and alcohol modifications of Cemadotin are also provided; see FIGS. 20, 22 and 23.

Drug loading on the PDC may range from 1 to 2 or more drugs per protein. Accordingly, 1, 2, 3, 4, 5, 6, 7, 8, 9 or 10 or more drug moieties may be covalently attached to the protein via a linker. Thus, compositions of PDCs may include collections of proteins conjugated with a one or more different drugs. The number of drugs per protein in preparations of PDCs may be characterized by conventional means—such as mass spectroscopy, ELISA assay, electrophoresis, and HPLC.

The drug may be used in their unmodified or modified form. Combinations of drugs in which some are unmodified and some are modified may be used. For example, the drug may be chemically modified. One form of chemical modification is the derivitisation of a carbonyl group—such as an aldehyde. According to one embodiment, the drug is modified to allow the incorporation of the linker.

ADCs

A preferred form of a PDC is an ADC. The ADCs described may selectively deliver an effective dose of a drug to a target tissue or cell—such as a target vascular tissue or cell.

The drug moiety of the ADC may not be cleaved from the linker until the ADC binds to its target cell or tissue.

In one embodiment, the ADCs described herein are not internalised into a cell since an antibody is chosen that cannot be internalised. Accordingly, the linker that is used in the ADC should be stable enough compared to the rate of antibody blood clearance but labile enough compared to the residence time of the antibody at the target site. From these considerations, a half-life of the linker in the region of about 1 hour to about 50 hours—such as about 10 to about 50 hours, about 20 to about 50 hours, about 30 hours to about 50 hours, about 30 hours to about 45 hours, about 35 hours to 45 hours, about 35 hours to 40 hours, or about 37 hours—may be acceptable, especially when vascular tissues or cells are targeted. A linker comprising a heterocyclic 1,3-substituted five- or six-member ring—such as a thiazolidine linker (or an analogue or derivative thereof)—is particularly suitable for this purpose, as disclosed herein. Advantageously therefore, the ADCs described herein may have improved lability and/or stability in vitro and/or in vivo which makes them particularly suitable for controlled drug release, especially at vascular tissues, cells and tumours.

Suitably, the ADC, inhibits, retards or prevents growth of a tumour when administered in a therapeutically effective amount.

A further aspect of the present invention relates to an ADC compound comprising an antibody covalently attached by a linker to one or more drug moieties, wherein said drug moiety comprises, consists or consists essentially of a carbonyl (eg. aldehyde) derivative of LU103793. According to this aspect of the invention, the ADC may or may not be internalised into a cell. If the ADC is internalised then before transport or delivery into a cell, the ADC is preferably stable and remains intact, i.e. the antibody remains linked to the drug moiety. Thus, the linkers are stable outside the target cell and may be cleaved inside the cell. Thus, an effective linker for internalisation may: allow intracellular delivery of the ADC and/or maintain the specific binding properties of the antibody and/or allow intracellular delivery of the ADC and/or is not cleaved until the ADC has been delivered or transported to its target site and/or maintains a cytotoxic, cytostatic or biocidal effect on the drug moiety. Suitable linkers are described herein.

Of course, the ADC compound comprising a drug moiety comprising, consisting or consisting essentially of a carbonyl (eg. aldehyde) derivative of LU103793 may be used in combination with a linker comprising a heterocyclic 1,3-substituted five- or six-member rings—such as a thiazolidine linker (or an analogue or derivative thereof)—as described herein.

The ADCs may be used in combination with an immunomodulator. An immunomodulator is a therapeutic agent that when present, alters, suppresses or stimulates the body's immune system. Typically, the immunomodulator will stimulate immune cells to proliferate or become activated in an immune response cascade. An example of an immunomodulator is a cytokine—such as a lymphokine, monokine, interleukin, or a signaling molecule—such as tumour necrosis factor (TNF) and interferons. Ths use of animmunomodulator may enhance the effectiveness of the ADC.

Preparation of PDCs

The PDCs may be prepared by several routes that are known in the art.

By way of example, PDCs may be prepared by reacting a nucleophilic group or an electrophilic group of a protein with a bivalent linker reagent, to form a protein-linker intermediate, via a covalent bond, followed by reaction with a drug moiety.

By of further example, the PDC may be prepared by reacting a nucleophilic group or an electrophilic group of a drug moiety with a linker reagent, to form a drug-linker intermediate, via a covalent bond, followed by reaction with the nucleophilic group or an electrophilic group of a protein.

Nucleophilic groups may include, but are not limited to: (i) N-terminal amine groups, (ii) side chain amine groups—such as lysine, (iii) side chain thiol groups—such as cysteine, isocysteine, (iv) side chain thiazinane groups—such as $\beta^2$-cysteine, homo-cysteine, homo-iso-cysteine; (v) side chain oxazolidine groups—such as serine (threonine), isoserine; (vi) side chain oxazirane groups—such as $\beta^2$-serine; homoserine, homo-iso-serine; (vii) side chain dioxane groups—such as diol-, di-hydroxybutiric acid; (viii) side chain dithiolane groups—such as 1,2-dimercaptopropionic acid; (ix) side chain dithiane groups—such as 2-carboxy-1, 3-propanedithiol, 2,4-dimercaptobutirric acid; (x) side chain oxathiolane groups—such as 3-hydroxy-2mercapto-propionic acid, 2-hydroxy-3-mercapto-propionic acid; (xi) side chain oxathiane groups—such as 3-hydroxy-2-(mercaptomethyl)-propanoic acid, 4-hydroxy-2-mercaptobutanoic acid, 2-hydroxy-4-mercaptobutanoic acid; (xii) side chain imidazolidine groups—such as 2,3-diaminopropionic acid; (xiii) side chain hexahydropyrimidine groups—such as 3-amino-2-(aminomethyl)-propionic acid and 2,4-diaminobutirric acid; (xiv) side chain glycerate groups—such as glyceric acid; (xv) side chain diol groups—such as i-hydroxybutiric acid; and (xvi) sugar hydroxyl or amino groups where the protein is glycosylated.

Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Certain antibodies have reducible interchain disulfides, i.e. cysteine bridges. Antibodies may be made reactive for conjugation with linker reagents by treatment with a reducing agent such as DTT. Each cysteine disulfide bridge will thus form, theoretically, two reactive thiol nucleophiles. Additional nucleophilic groups can be introduced into antibodies through the reaction of lysines with 2-iminothiolane resulting in conversion of an amine into a thiol.

Cysteine residues can also be introduced at the N-termini of antibody molecules by mutagenesis of nucleic acid sequences intended for expression in cell lines. If desired, spacers of one or more amino acid residues can be positioned between the N-terminal cysteine and the antibody sequence. The spacer can be, for example one or more glycine residues. Preferably, the spacer is one glycine residue.

PDCs may also be produced by modification of the protein to introduce electrophilic moieties, which can react with nucleophilic substituents on the linker reagent or drug. The sugars of glycosylated proteins may be oxidized, e.g. with periodate oxidizing reagents, to form carbonyl groups—such as aldehyde or ketone groups—which may react with the amine group of linker reagents or drug moieties. The resulting imine Schiff base groups may form a stable linkage, or may be reduced, e.g. by borohydride reagents to form stable amine linkages.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Reactive nucleophilic groups may be introduced on the macrocyclic depsipeptide compounds by standard functional group interconversions.

A further aspect relates to the direct reaction between a protein comprising a terminal precursor—such as an N-terminal cysteine (eg. at position 1)—and a carbonyl (eg. aldehyde) containing molecule—such as a drug. Accordingly, there is also provided a method of obtaining a PDC comprising the step of reacting the protein comprising a terminal precursor with a carbonyl (eg. aldehyde) containing molecule.

A further aspect relates a method of preparing a PDC comprising the steps of: (a) providing a protein comprising a terminal precursor moiety—such as an N-terminal cysteine moiety; (b) incubating the protein obtained from step (a) with a carbonyl (eg. aldehyde) containing molecule—such as a drug; and (c) obtaining a PDC. As the skilled person will appreciate, steps (a) and (b) can be preformed in reverse order. Thus, the method can comprise the steps of (a) providing the carbonyl (eg. aldehyde) containing molecule—such as a drug; (b) incubating the molecule from step (a) with a protein comprising a terminal precursor moiety—such as an N-terminal cysteine moiety; and (c) obtaining a PDC.

According to one embodiment, the PDC is prepared in situ.

Screening for PDCs

Transgenic animals and cell lines are particularly useful in screening PDCs that have potential as prophylactic or therapeutic treatments of diseases or disorders. Screening for a useful PDC may involve administering the candidate PDC over a range of doses to the transgenic animal, and assaying at various time points for the effect(s) of the PDC on the disease or disorder being evaluated.

The drug may be administered prior to or simultaneously with exposure to an inducer of the disease, if applicable. Candidate PDCs may be screened serially or individually, or in parallel under medium or high-throughput screening formats.

One may assess the growth inhibitory effects of a test PDC on cell lines derived from a transgenic animal. According to this assay, the cells may be treated with a test compound at various concentrations for a defined number of days and stained. Incubation with the compound may show a growth inhibitory effect on the cell line.

In Vitro Cell Proliferation Assays

The activity of an PDC may be measured using methods known in the art and will depend on the choise of PDC. If the protein is an antibody then the activity of the ADC may be determined by: exposing cells having an antigen or receptor protein to the antibody of the ADC in a cell culture medium; culturing the cells; and measuring the viability of the cell in the presence of the ADC. Cell-based in vitro assays may be used to measure viability (eg. proliferation, cytotoxicity and/or induction of apoptosis of the PDC). Suitable methods and kits are described in U.S. Pat. No. 5,583,024 and *J. Immunol. Meth.* (1993) 160:81-88

Treatment

The PDCs described herein may be used to treat disease. The treatment may be therapeutic and/or prophylactic treatment, with the aim being to prevent, reduce or stop an undesired physiological change or disorder. The treatment may prolong survival as compared to expected survival if not receiving treatment.

The disease that is treated by the PDC may be any disease that might benefit from treatment. This includes chronic and acute disorders or diseases including those pathological conditions which predispose to the disorder. One particular disease that is applicable to treatment by the present invention is cancer—such as cancer that can be treated via the targeted destruction of the established tumour vasculature. Non-limiting examples of cancers that may be treated include benign and malignant tumours; leukemia and lymphoid malignancies, including breast, ovarian, stomach, endometrial, salivary gland, lung, kidney, colon, thyroid, pancreatic, prostate or bladder cancer. The disease may be a neuronal, glial, astrocytal, hypothalamic or other glandular, macrophagal, epithelial, stromal and blastocoelic disease; or inflammatory, angiogenic or an immunologic disease. An exemplary disease is a solid, malignant tumour.

The term "cancer" and "cancerous" is used in its broadest sense as meaning the physiological condition in mammals that is typically characterized by unregulated cell growth. A tumour comprises one or more cancerous cells. Examples of cancer include, but are not limited to, carcinoma, lymphoma, blastoma, sarcoma, and leukemia or lymphoid malignancies. Further examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, gastrointestinal stromal tumour (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the dosage of a PDC will depend on an array of different factors—such as the type of disease to be treated, the severity and course of the disease, whether the molecule is administered for preventive or therapeutic purposes, previous therapy, the patient's clinical history and response to the protein, and the discretion of the attending physician.

The molecule may be administered to the patient at one time or over a series of treatments. Depending on the type and severity of the disease, between about 1 ug/kg to 15 mg/kg of drug may be used as an initial candidate dosage for administration to the patient, whether, for example, by one or more separate administrations, or by continuous infusion. A typical daily dosage might range from about 1 ug/kg to 100 mg/kg or more. An exemplary dosage of drug may be in the range of about 0.1 to about 10 mg/kg of patient weight.

When treating cancer, the therapeutically effect that is observed may be a reduction in the number of cancer cells; a reduction in tumour size; inhibition or retardation of cancer cell infiltration into peripheral organs; inhibition of tumour growth; and/or relief of one or more of the symptoms associated with the cancer.

In animal models, efficacy may be assessed by physical measurements of the tumour during the treatment, and/or by determining partial and complete remission of the cancer. For cancer therapy, efficacy can, for example, be measured by assessing the time to disease progression (TTP) and/or determining the response rate (RR).

Pharmaceutical Compositions

The PDCs described herein may be in the form of pharmaceutical compositions which may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration the compositions may be administered in the form of tablets or lozenges which can be formulated in a conventional manner.

The PDC may be administered in the form of a pharmaceutically acceptable or active salt. Pharmaceutically-acceptable salts are well known to those skilled in the art, and for example, include those mentioned by Berge et al, in J. Pharm. Sci., 66, 1-19 (1977). Salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The formulations may be packaged in unit-dose or multi-dose containers, for example sealed ampoules and vials, and may be stored in a freeze-dried (lyophilized) condition requiring only the addition of the sterile liquid carrier, for example water, for administration. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

Combination Therapy

A PDC may be combined in a pharmaceutical combination formulation, or dosing regimen as combination therapy, with a second compound having therapeutic properties. The second compound of the pharmaceutical combination formulation or dosing regimen preferably has complementary activities to the PDC of the combination such that they do not adversely affect each other.

The second compound may be selected from the group consisting of another protein, antibody, antigen-binding fragment thereof, a drug, a toxin, an enzyme, a nuclease, a hormone, an immunomodulator, an antisense oligonucleotide, an siRNA, a boron compound, a photoactive agent, a dye and a radioisotope or a combination of two or more thereof.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

Kits

In another embodiment, a kit or an article of manufacture, containing a PDC and materials useful for the treatment of the disorders described herein is provided. The article of manufacture comprises a container and a label or package insert on or associated with the container. Suitable containers include, for example, bottles, vials, syringes, or blister pack. The containers may be formed from a variety of materials such as glass or plastic. The container holds a PDC composition which is effective for treating the condition and may have a sterile access port (for example the container may be an intravenous solution bag or a vial having a stopper pierceable by a hypodermic injection needle). At least one active agent in the composition is a PDC. The label or package insert indicates that the composition is used for treating a condition of choice, such as cancer.

The kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Substituents

The chemical compounds described herein may comprises substituents. In particular, the compounds may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen (e.g. fluoro) substituents.

Chemical Synthesis

The compounds described herein may be prepared by chemical synthesis techniques.

It will be apparent to those skilled in the art that sensitive functional groups may need to be protected and deprotected during synthesis of a compound. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be epimerised, for example if a base is used in a reaction with a substrate having an optical centre comprising a base-sensitive group. It should be possible to circumvent potential problems such as this by choice of reaction sequence, conditions, reagents, protection/deprotection regimes, etc. as is well-known in the art.

The compounds and salts of the invention may be separated and purified by conventional methods.

General Techniques

The practice of the present invention employs, unless otherwise indicated, conventional methods of chemistry, biochemistry, molecular biology, cell biology, genetics, immunology and pharmacology, known to those of skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

The invention will now be further described by way of Examples, which are meant to serve to assist one of ordinary skill in the art in carrying out the invention and are not intended in any way to limit the scope of the invention.

EXAMPLES

Example 1

Use of Thiazolidine as a Novel Linker for the Controlled Drug Release from an ADC Materials & Methods Synthesis of protein-fluorophore conjugates via a thiazolidine linker. A DMSO solution (70 µL) of fluorophore-N-hydroxisuccinimide reagent (0.4 mg, 0.576 µmol, 20-40 equiv. for fluorescein; 0.33 mg, 0.576 µmol, 20-40 equiv. for coumarine) was added to a PBS solution of either BSA or IgG F8 (2 mL, 1 to 2 mg/mL concentration) and incubated at 4° C. for 16 hours. The protein-fluorophore conjugates were then purified from the free fluorophore over a PD-10 column (GE-Healthcare). Quality of the Protein-Fluorophore Conjugate.

Quality of the protein-fluorophore conjugate. Protein-fluorophore conjugates were analyzed by SDS-PAGE under non-reducing conditions using the Invitrogen PAGE system following manufacturer instructions. The gels were first analyzed under the ethidium-bromide lamp and then stained with Coomassie blue. Conjugates mass was measured on an AB4800 MALDI-TOF/TOF, after mixing the protein-conjugates with sinapinic acid matrix.

Conjugate loading and dye release experiments. The labeling ratio was estimated spectroscopically by measuring the absorbance of peaks eluting from a size exclusion column at retention volume expected for proteins. The absorbance at 280 nm was used for the protein ($\epsilon_{BSA}$=43824 $M^{-1}$ $cm^{-1}$, and $\epsilon_{IgG}$=189498 $M^{-1}$ $cm^{-1}$), after correction for the absorption of the fluorophore), 502 nm for the fluorescein ($\epsilon_F$=68000 M$^{-1}$ cm$^{-1}$), or 420 nm for the coumarine ($\epsilon_C$=47713 M$^{-1}$ cm$^{-1}$). The following formula was used for the quantification: (D/P)=$A_D$*$\epsilon_D$/[($A_{280}$−0.3*$A_D$)*($\epsilon_P$)], where D and P represent the dye and protein respectively.

Results

The ability of the thiazolidine moiety to act as a labile linker was tested on conjugates carrying BSA and a fluorophore at the extremities. The number of free lysines available (60) makes this protein ideal for free amine acylation as a conjugation strategy. The reaction was performed by dissolving the pre-activated fluorophore-containing thiazolidine (shown below, carboxyfluorescein on the left and diethylamino coumarin on the right and both bearing the thiazolidine moiety) in DMSO, followed by addition of the protein solution in buffer. The reaction was then purified by gel filtration and the quality of the conjugate assessed by SDS gel electrophoresis.

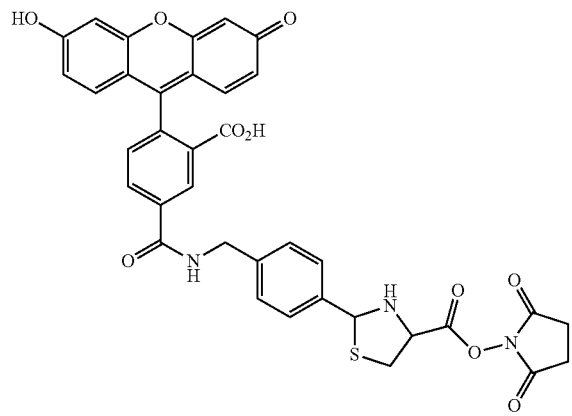

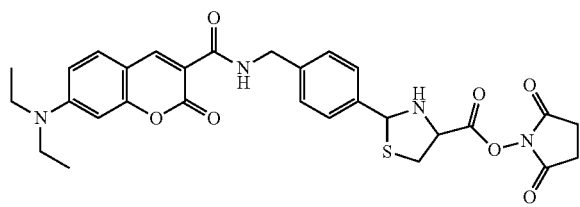

Figure 2:
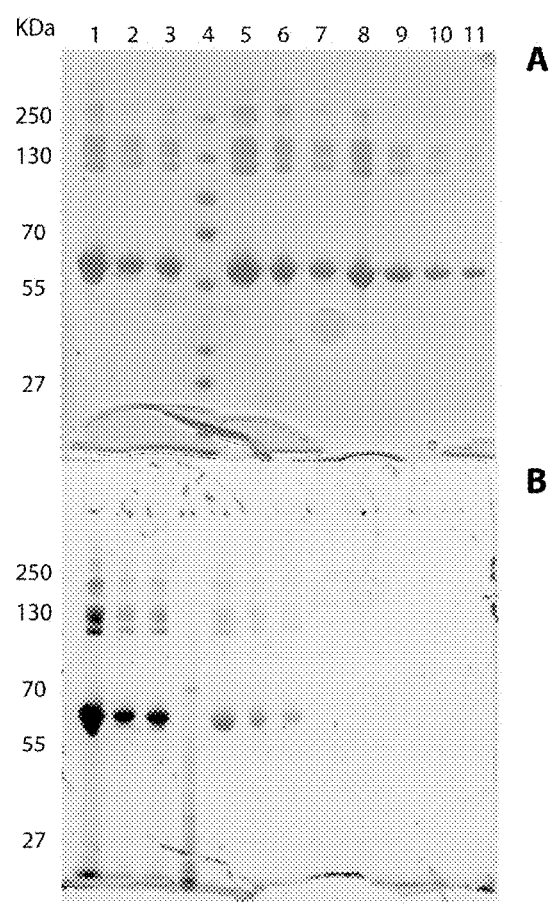

Imaging of the gel by ethidium bromide fluorescence revealed the presence of both fluorescein and coumarine BSA-conjugates (FIG. 2B, lower panel): the lower intensity of the coumarine conjugates is due both to a lower labeling degree and to the fluorescence filter used. Coomassie staining confirmed that the products are BSA conjugates and that their concentration is approximately equal in both labeling experiments. (FIG. 2A, upper panel).

Figure 3:
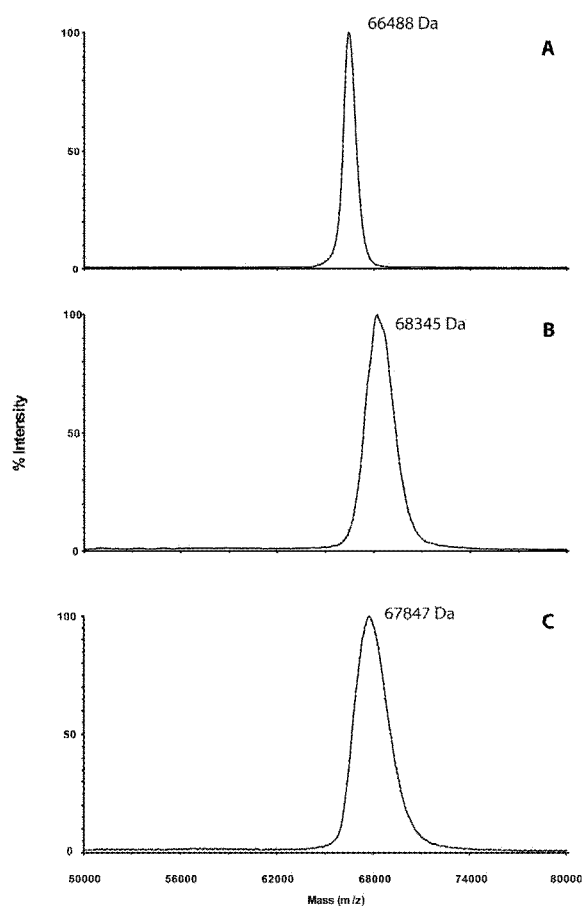

The quality of the conjugates was assessed also by mass spectrometry, and the modifications degree was 3 for both fluorophores. (FIG. 3).

Figure 4:
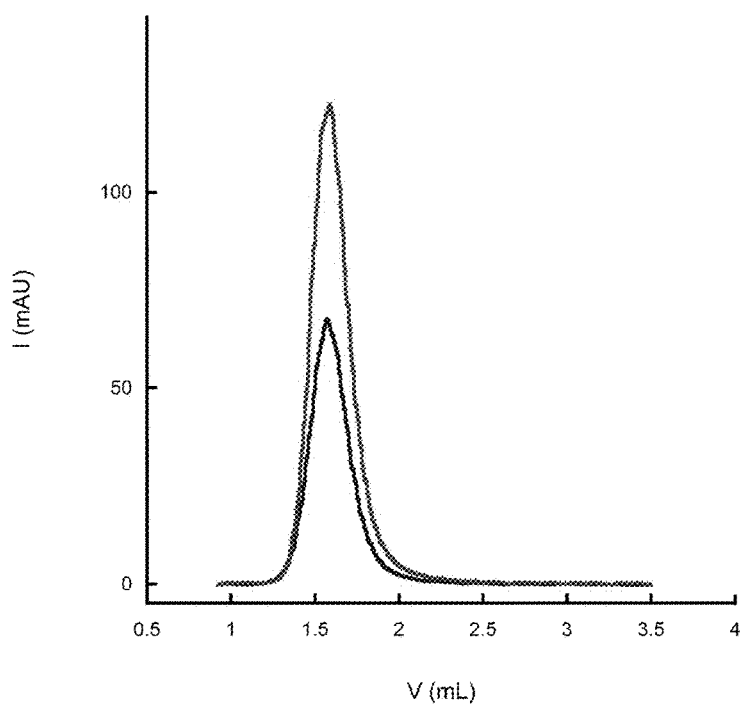

The fluorophore loading on the protein molecule was also determined by UV spectroscopy. In FIG. 4, an example for the fluorescein conjugate is reported: the co-elution of the protein (blue curve, 280 nm) with the fluorophore (red curve, 502 nm) on a size exclusion column is a clear indication of a covalent conjugate formed between the protein and the dye. Moreover, the loading determined with this technique was in good agreement with the MS results.

Figure 5:
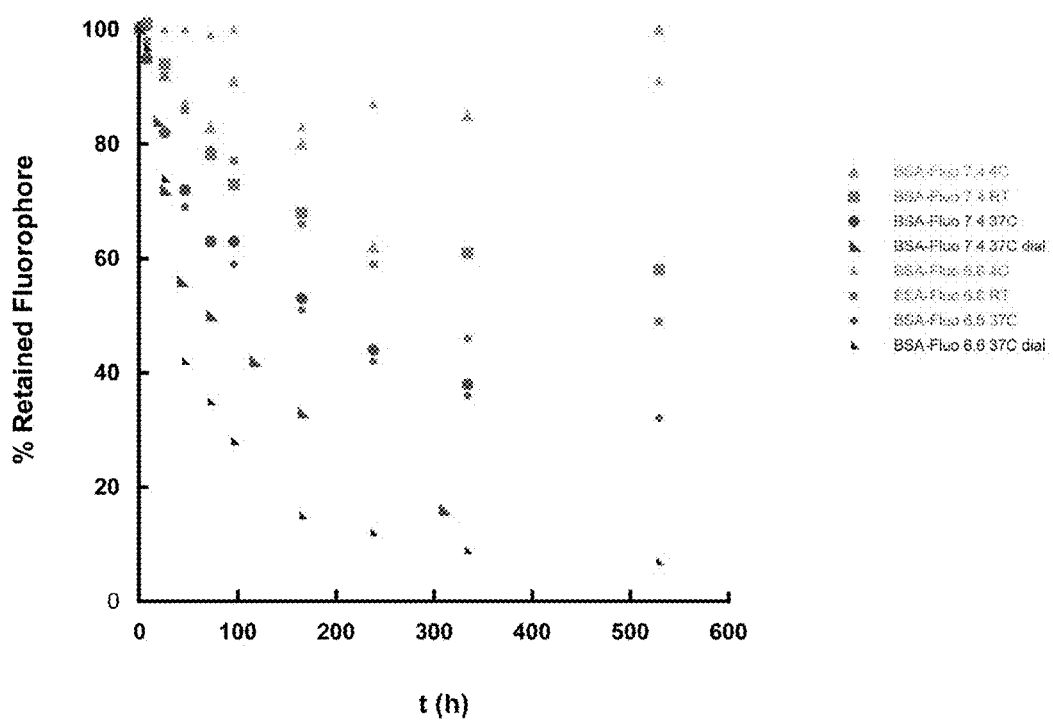

The decrease in intensity with time of the peak at 502 nm is used to determine the fluorescein release from the conjugate. The BSA-fluorescein conjugate was incubated at temperatures ranging from 37° C. to 4° C., both at pH 6.6 and 7.4 in an eppendorf tube and in a dialysis bag. The rate of fluorophore release increased with the temperature. Experiments carried out in a dialysis bag show faster release, suggesting that the constant driving force provided by the dialysis is capable of shifting the hydrolysis to the end product. On the contrary, pH seems to play a minor role in the release influence. pH 6.6 recorded the fastest half-life of 37 hours (FIG. 5).

Figure 6:
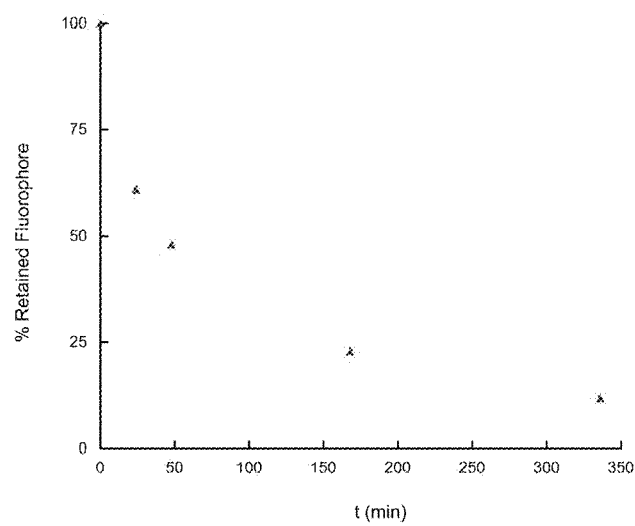

Additionally a test experiment was performed with IgG F8 antibody, and the half-life recorded was 34 hours, in perfect agreement with the BSA-fluorescein experiment (FIG. 6).

Conclusions

Thiazolidine proved to be a suitable moiety to link both BSA and antibodies to test fluorophores. The half-lives recorded at different pH fall in a range that is suitable for targeted drug delivery using ADCs.

The agreement between UV and MS data allow an extension of the methods used for the release determination, especially important in the case of non-UV active payloads such as LU103793. Finally, development of specific antibodies against LU103793 will make ELISA analysis for release studies easier for LU103793-antibody conjugate possible.

Example 2

Aldehyde Derivatives of LU103793 are Potent Cytotoxins that can be Coupled to Antibodies Materials and Methods HEK293T cells were grown in RPMI (Gigbo-Invitrogen) medium supplemented with 10% FCS and antibiotics and maintained at 37° C. in 5% $CO_2$.

For the in vitro toxicity assay 30000 cells/well (final volume 100 µl) were seeded in a 96 well plate with a defined peptide dilution (by adding 1.5 µl of peptide solution to 500 µl of cell suspension) and incubated at 37° C. in 5% $CO_2$.

After ~72 hours, cell viability was measured using the "Cell Titer 96®Aqueous One Solution Cell Proliferation Assay" (Promega), performed according to the manufacturers instruction. Briefly: 20 µl of MTS solution were added to each well, the plate was then incubated at 37° C. for 2 hour. The read out of the assay is the absorbance at 490 nm.

The experiments were then extended to F9 and HL60 cells in the same manner.

Results

Figure 7:
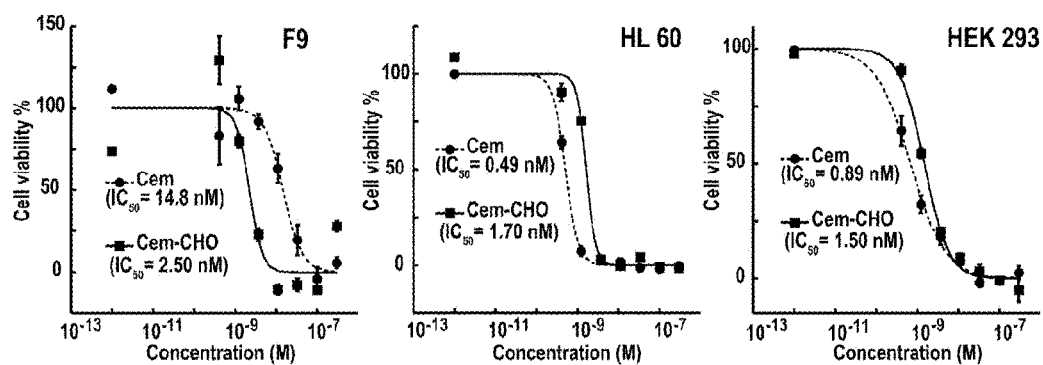

The cytotoxicity of both Cemadotin (Cem) and Cemadotin aldehyde (Cem-CHO) was determined by the MTS colorimetric cell proliferation assay. The direct correlation between colorimetric outcome and viable cells, allows direct measurement of $IC_{50}$. Both polypeptides showed comparable sub-nanomolar cytotoxicity (FIG. 7) in all three cell types assayed.

Conclusions

Previous experiments in our group showed that the activity of LU103793 is very sensitive to modifications. Surprisingly the introduction of an aldehyde moiety at the C-terminus of the polypeptide is not detrimental for activity, and allows a useful handle for further modification.

Example 3

Chemoselective, In Situ Thiazolidine Synthesis: Reaction Between n-terminal Cysteine Containing Protein and a Carbonyl Materials and Methods In situ thiazolidine synthesis: Recombinant Cys-EDB (1 mg, 100 nmol) was reduced with 20 mM DTT for 1 h in PBS buffer. The amino acid sequence of Cys-EDB is shown in FIG. 9. After removing the reducing agent by dialysis, the protein was incubated with the aldehyde containing fluorescein (0.5 mg, 1.0 µmol, 10 equiv., 5 mM DMF solution) at room temperature for 16 h. The fluorophore-protein conjugate was then purified by gel filtration on a PD-10 column (GE Healthcare).

Quality of the protein-fluorophore conjugate: Protein-fluorophore conjugates were analyzed by SDS-PAGE under non-reducing conditions using the Invitrogen PAGE system, following manufacturer instructions. The gels were first analyzed under using the ethidium-bromide lamp and then stained with Coomassie blue.

Results

Figure 10:
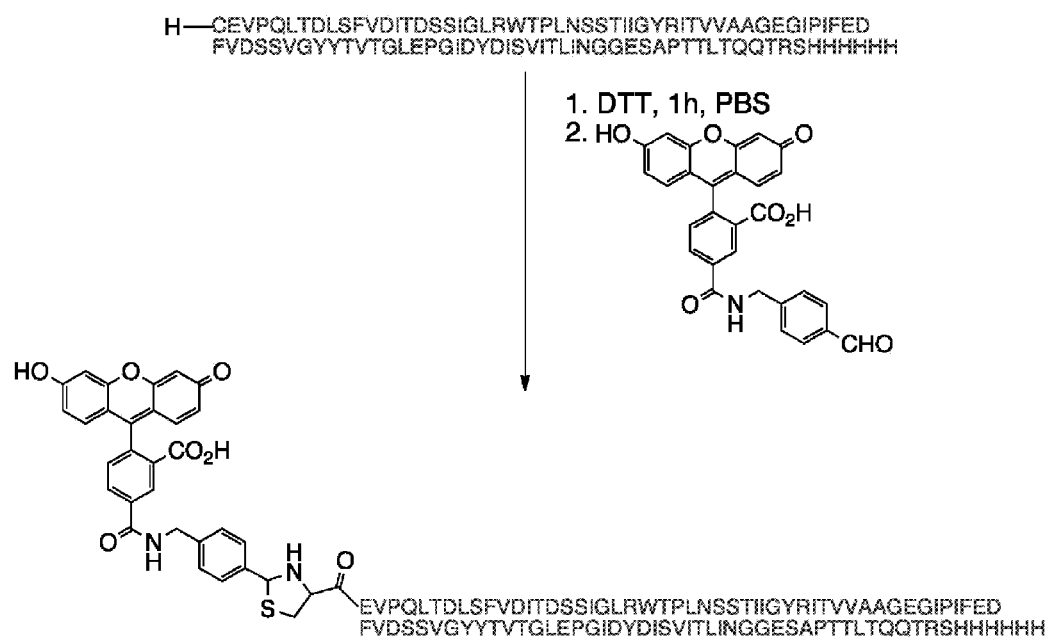
FIG. 10 shows a reaction scheme for the in-situ site specific synthesis of a thiazolidine linker.

A cysteine amino acid was added to the N-terminus of EDB to allow its specific modification (Cys-EDB). After reduction of the N-terminal cysteine with dithiothreitol (DTT), the protein was reacted with an excess of the fluorescein containing aldehyde for 16 h (FIG. 10).

After gel filtration, the reaction was analyzed by SDS gel electrophoresis under non-reducing conditions. Imaging of the gel using ethidium bromide first and Coomassie staining after, confirmed the presence of the fluorescein-protein conjugate via the thiazolidine linker (FIG. 11, lane 1); Interestingly, the band corresponding to the dimerized starting material (approx. 22 KDa) is absent, showing the efficiency of the thiazolidine formation process.

Conclusions

The possibility to selectively control post-translational protein modification is of great value. It allows to better correlate their structure and function: the thiazolidine synthesis belongs to this category of reactions. The results presented show that it is possible to selectively derivatize with a thiazolidine moiety a protein containing an N-terminal cysteine by reaction with an aldehyde-containing compound. The corresponding synthesized heterocycle can be further used, due to its stability properties as described herein.

Example 4

In Situ Thiazolidine Synthesis in Antibody Molecules

In antibodies and proteins 1,2-aminothiol functions are naturally provided by N-terminal cysteines: several strategies are known to access them (Muir, T. W. Annu. Rev. Biochem 2003, 72, 249; Casi, G.; Hilvert, D. Curr. Opin. in Struct. Biol. 2003, 13, 589). However they all suffer from poor proteolytic efficiency, and troublesome purification procedures. We envisaged that introducing a cysteine as the first amino acid after the leader peptide in an antibody sequence might provide an N-terminal cysteine containing protein upon secretion during mammalian cell production. Moreover the influence of glycine spacers between cysteine and the antibody sequence was tested (FIG. 12 a,b). We focused our study on the F8 antibody, specific to the alternatively-spliced EDA domain of fibronectin, a marker of tumor angiogenesis. The antibody was used in the diabody format (Holliger, P.; Prospero, T.; Winter, G. PNAS 1993, 90, 6444) thus providing two cysteines as potential precurson moieties per antibody molecule under physiologic conditions. Our aldehyde source is Cem-CHO, a potent cytotoxic analogue of Cemadotin previously described in this patent application (FIG. 12c).

Antibodies with different linkers were produced in Chinese Hamster Ovary cells (CHO cells). Our strategy consisted in introducing four, one or no glycine spacers between the N-terminal cysteine and the F8-diabody sequence. Four glycines prevented protein production, however one glycine or no glycines were tolerated and expressed the desired proteins (FIG. 13d, 14d). SDS PAGE shows that both under non-reducing and reducing conditions the proteins run as monomers (FIG. 13d, 14d lanes 7 and 8): that could be a consequence of cysteine being hidden in the antibody quaternary structure or simply chemically modified. ESI-MS analysis confirmed the latter assumption, showing no presence of the desired protein mass probably as a consequence of the N-terminal cysteine reacting with low molecular weight thiols or aldehydes (FIG. 13a, 14a). Treatment with 10 mM DTT as reducing agent first and with 400 mM MeONH$_2$ subsequently afforded the desired protein (FIGS. 13b, 14b). The N-terminal cysteine was then reacted with Cemadotin aldehyde (ca 100 equiv.) in AcOK pH 4.5 in the presence of 1 mM reducing agent (DTT or TCEP). After 2.5 days both proteins showed conversion to the desired conjugate with yields in excess of 90% as confirmed both by ESI-MS and SDS PAGE (FIGS. 13c-d, 14c-d) with a 55% overall yield. The ADCs were purified over Hitrap desalting cartridges, and analytical size exclusion chromatography showed pure conjugates (FIG. 13e, 14e).

Both ADCs were tested for Cemadotin aldehyde release at 37° C. by tandem LC-MS/MS spectroscopy (FIG. 15). The half-life of the conjugates was 45 hours and the total amount of released drug was estimated to be 65% of the total expected. Samples stored at 4° C. and −80° C. were analyzed for ADC stability under these storage conditions and practically showed no drug release over the course of one week for the Cys-Gly (F8) conjugate. These results confirm that the thiazolidine linker may be suitable for the delivery of toxic moieties in vivo, given its slow release rate providing that the antibody used for therapy experiments will have a long half-life in serum, sufficient to localize the drug and achieve the desired disruption of the tumor blood vessels.

Methods: Production of N-terminal Cysteine Containing Antibodies.

Material and Methods:

Cloning was performed in pcDNA3.1 vector, and either transient gene expression or stable cell lines were used to produce the different antibodies.

```
Cloning strategy:
H-Cys-F8
HindIII - Leader Sequence - Cys - VH (F8) - 5 aa (linker) -
VL (F8) - STOPSTOP - NotI
DNA Sequence
                                                    (SEQ ID NO: 1)
CCCaagcttGTCGACCATGGGCTGGAGCCTGATCCTCCTGTTCCTCGTCGCTGTGGC TACAGGTgtgcacTCGTGCGAGGTGCAGCTGTTGGAGTCTGGGGGAGGCTTGGTACA

GCCTGGGGGGTCCCTGAGACTCTCCTGTGCAGCCTCTGGATTCACCTTTAGCCTGT
```

-continued

```
TTACGATGAGCTGGGTCCGCCAGGCTCCAGGGAAGGGGCTGGAGTGGGTCTCAGC

TATTAGTGGTAGTGGTGGTAGCACATACTACGCAGACTCCGTGAAGGGCCGGTTCA

CCATCTCCAGAGACAATTCCAAGAACACGCTGTATCTGCAAATGAACAGCCTGAGA

GCCGAGGACACGGCCGTATATTACTGTGCGAAAAGTACTCATTTGTATCTTTTTGAC

TACTGGGGCCAGGGAACCCTGGTCACCGTCTCGAGTGGCGGTAGCGGAGGGGAAA

TTGTGTTGACGCAGTCTCCAGGCACCCTGTCTTTGTCTCCAGGGGAAAGAGCCACC

CTCTCCTGCAGGGCCAGTCAGAGTGTTAGCATGCCGTTTTTAGCCTGGTACCAGCA

GAAACCTGGCCAGGCTCCCAGGCTCCTCATCTATGGTGCATCCAGCAGGGCCACT

GGCATCCCAGACAGGTTCAGTGGCAGTGGGTCTGGGACAGACTTCACTCTCACCAT

CAGCAGACTGGAGCCTGAAGATTTTGCAGTGTATTACTGTCAGCAGATGCGTGGTC

GGCCGCCGACGTTCGGCCAAGGGACCAAGGTGGAAATCAAAtaaGCGGCCGCAAAA

GGAAAA
```

Protein sequence
(SEQ ID NO: 2)
```
MGWSLILLFLVAVATGVHSCEVQLLESGGGLVQPGGSLRLSCAASGFTFSLFTMSWVR

QAPGKGLEWVSAISGSGGSTYYADSVKGRFTISRDNSKNTLYLQMNSLRAEDTAVYYC

AKSTHLYLFDYWGQGTLVTVSSGGSGGEIVLTQSPGTLSLSPGERATLSCRASQSVSM

PFLAWYQQKPGQAPRLLIYGASSRATGIPDRFSGSGSGTDFTLTISRLEPEDFAVYYCQ

QMRGRPPTFGQGTKVEIK
```

Primers(italic part responsible for annealing)
1, forward
(SEQ ID NO: 3)
5' TGCGAGGTGCAGCTGTTGGAGTCTGG 3'

$T_m$ = 79.2° C. Length (base pairs) = 26

2, forward
(SEQ ID NO: 4)
5' GTTCCTCGTCGCTGTGGCTACAGGTgtgcacTCGTGCGAGGTGCAGCTGTTGGAG 3'

$T_m$ = 94.4° C. Length (base pairs) = 55

3, forward
(SEQ ID NO: 5)
5' CCCAAGCTTGTCGACCATGGGCTGGAGCCTGATCCTCCTGTTCCTCGTCGCTGTGGC3'

$T_m$ = 95.8° C. Length (base pairs) = 57

Back
(SEQ ID NO: 6)
5' TTTTCCTTTTGCGGCCGCTTATTTGATTTCCACCTTGGTCCC 3'

$T_m$ = 85.3° C. Length (base pairs) = 42

H-Cys-Gly-F8
HindIII -Leader Sequence - Cys - Gly - VH (F8) - 5 aa (linker) -
VL (F8) -STOPSTOP - NotI
DNA Sequence
(SEQ ID NO: 7)
```
CCCaagcttGTCGACCATGGGCTGGAGCCTGATCCTCCTGTTCCTCGTCGCTGTGGC TACAGGTgtgcacTCGTGCGGTGAGGTGCAGCTGTTGGAGTCTGGGGGAGGCTTGGT

ACAGCCTGGGGGGTCCCTGAGACTCTCCTGTGCAGCCTCTGGATTCACCTTTAGCC

TGTTTACGATGAGCTGGGTCCGCCAGGCTCCAGGGAAGGGGCTGGAGTGGGTCTC

AGCTATTAGTGGTAGTGGTGGTAGCACATACTACGCAGACTCCGTGAAGGGCCGGT

TCACCATCTCCAGAGACAATTCCAAGAACACGCTGTATCTGCAAATGAACAGCCTGA

GAGCCGAGGACACGGCCGTATATTACTGTGCGAAAAGTACTCATTTGTATCTTTTTG

ACTACTGGGGCCAGGGAACCCTGGTCACCGTCTCGAGTGGCGGTAGCGGAGGGG
```

-continued

```
AAATTGTGTTGACGCAGTCTCCAGGCACCCTGTCTTTGTCTCCAGGGGAAAGAGCC

ACCCTCTCCTGCAGGGCCAGTCAGAGTGTTAGCATGCCGTTTTTAGCCTGGTACCA

GCAGAAACCTGGCCAGGCTCCCAGGCTCCTCATCTATGGTGCATCCAGCAGGGCC

ACTGGCATCCCAGACAGGTTCAGTGGCAGTGGGTCTGGGACAGACTTCACTCTCAC

CATCAGCAGACTGGAGCCTGAAGATTTTGCAGTGTATTACTGTCAGCAGATGCGTG

GTCGGCCGCCGACGTTCGGCCAAGGGACCAAGGTGGAAATCAAAtaaGCGGCCGCA

AAAGGAAAA

Protein sequence
                                                   (SEQ ID NO: 8)
MGWSLILLFLVAVATGVHSCGEVQLLESGGGLVQPGGSLRLSCAASGFTFSLFTMSWV

RQAPGKGLEWVSAISGSGGSTYYADSVKGRFTISRDNSKNTLYLQMNSLRAEDTAVYY

CAKSTHLYLFDYWGQGTLVTVSSGGSGGEIVLTQSPGTLSLSPGERATLSCRASQSVS

MPFLAWYQQKPGQAPRLLIYGASSRATGIPDRFSGSGSGTDFTLTISRLEPEDFAVYYC

QQMRGRPPTFGQGTKVEIK

Primers (italic part responsible for annealing)
1, forward
                                                   (SEQ ID NO: 9)
5' TGCGGTGAGGTGCAGCTGTTGGAGTCTGG 3'

T_m = 82.8° C. Length (base pairs) = 29

Primer 2, forward
                                                   (SEQ NO: 10)
5' GTTCCTCGTCGCTGTGGCTACAGGTgtgcacTCGTGCGGTGAGGTGCAGCTG 3'

T_m = 94.6° C. Length (base pairs) = 52

Primer 3, forward
                                                   (SEQ ID NO: 11)
5' CCCAAGCTTGTCGACCATGGGCTGGAGCCTGATCCTCCTGTTCCTCGTCGCTGTGGC3'

T_m = 95.8° C. Length (base pairs) = 57

Primer back
                                                   (SEQ ID NO: 12)
5' TTTTCCTTTTGCGGCCGCTTATTTGATTTCCACCTTGGTCCC 3'

T_m = 85.3° C. Length (base pairs) = 42
```

Conjugation: After production of the N-terminal cysteine-containing antibody, the preparation was treated with DTT (10 mM) first and then with MeONH$_2$ (400 mM final concentration) in order to restore a functional cysteine, partially modified by cytosol small molecules. After purification the functional protein was incubated with cemadotin aldehyde at different concentrations (1-4 mM) at pH 4.5 (100 mM AcOK) with 1 mM reductant (DTT or TCEP) and 10% EtOH. The reaction was monitored by LC-ESI/MS after 2.5 days. The protein was purified by gel filtration (HiTrap desalting columns, PBS) and the desired product stored at −80° C.

Release: The Cemadotin-F8 conjugates were incubated at 37° C. in PBS. Aliquots were analyzed by tandem LC-ESI/MS/MS spectrometry in order to assess the free drug released from the conjugate in solution.

Conclusions:

Incorporation of cysteine as a first amino acid immediately before the leader sequence of an antibody allows the secretion of N-terminal containing cysteine antibodies in moderate to good yields. This novel class of antibodies allows the expansion of the capabilities of antibody modification and functional gain. Both cysteine and cysteine-glycine containing antibodies underwent thiazolidine formation reaction with aldehyde containing highly cytotoxic cemadotin derivative, with practically full conversion. The purified conjugate showed the release of >65% of the total expected toxin with rates compatible with antibody localization kinetics at the tumor site. In the case of our highly potent aldehyde-drug derivative (Cem-CHO), and of the N-terminal cysteine containing antibody, the thiazolidine linker represents one of the few examples of a traceless linker applied to ADC. The generality of the traceless thiazolidine labeling technology, the site selective modification and the optimal release rates of the drug from the conjugate are outstanding prerequisites for the application of those novel ADC in preclinical and clinical studies.

Example 5

Chemoselective Incorporation of "N-terminal Cysteine-like" Functionality in the Middle of an Antibody Sequence Cysteine represents an extremely appealing amino acids for its unique reactivity and is used in site selective modification strategies both in proteins and antibodies. We have reported the production of C-terminal modified F8 antibodies incorporating cysteines (Truessel, S.; Dumelin, C.; Frey, K.; VIIIa, A.; Buller, F.; Neri, D. Bioconjugate Chem. 2009, 20, 2286), and their use as potential therapeutic agents. Our interest in thiazolidine as a linker requires the presence of an N-terminal cysteine-like functional group; therefore we envisaged taking advantage of a C-terminal cysteine amino acid in an antibody to append, site selectively, an N-terminal cysteine-like functional group. We designed a bifunctional linker bearing a maleimide ring and a thiazolidine protected cysteine (FIG. 16a).

We focused on the F8 antibody in the diabody format that was reduced with 1 mM TCEP to undergo addition reaction to the maleimide unit of the bidentate linker (FIG. 16b). The reaction is selective and quantitative as shown by ESI-MS (FIG. 17b). The thiazolidine group can then directly be treated with excess of MeONH$_2$ (400 mM final concentration, pH 3-4) to afford the desired N-terminal cysteine-like functionality (FIG. 17c). The modified antibody, after purification, was reacted with Cemadotin aldehyde (ca 100 equiv.) in AcOK pH 4.5 in the presence of 1 mM reducing agent (DTT or TCEP). After 2.5 days the desired conjugate was obtained with conversions in excess of 95% as confirmed by ESI-MS (FIG. 17d), and an overall yield of 40% with respect to the starting oxidized antibody. The ADC was purified over Hitrap desalting cartridges, and analytical size exclusion chromatography showed a pure conjugate (FIG. 17e).

Also in this case the conjugate was tested for Cemadotin aldehyde release at 37° C. by tandem LC-MS/MS spectroscopy (FIG. 18). The half-life of the conjugate was calculated around 12 hours with a global release of 94% with respect to the maximum expected.

Materials and Methods

Incorporation of N-terminal cysteine like functionality: F8 diabody containing a C-terminal cysteine (dB-F8-Cys) (0.73 mg/mL, 2 mL, PBS) was reduced with TCEP (20 equiv., 4° C., 9 h). Maleimide dissolved in water was subsequently added (40 equiv.) and allowed to react 15 hours. After that MeO-NH$_2$ was added (final concentration 400 mM, pH 3-4), and the reaction incubated overnight. Then the mixture was purified by gel-filtration (HiTrap desalting cartridge, 100 mM AcOK pH 4.5), the desired protein concentrated to 1-2 mg/mL with vivaspin (10 KDa cutoff), reduced with DTT (1 mM final concentration) for 15 h, and incubated with 4 mM final concentration of Cemadotin aldehyde for thiazolidine formation reaction. The reaction was judged to be complete after 48 h, the conjugate was purified by gel filtration HiTrap desalting cartridge, (PBS) and drug release was assessed by incubation at 37° C. under physiological conditions.

Conclusions:

The example reported in this embodiment represents the first time an "N-terminal like functionality" has been chemically introduced in an antibody and in a protein in general. The process is well tolerated by antibodies, and affords a novel chemoselective method by which antibodies and proteins can expand their reactivity: an overall yield of 40% in a protein modification method involving four chemical steps and two purifications is remarkable. The shorter half-life observed might be due to the different chemical environment surrounding the linker. Moreover that results shows that thiazolidine stability might be finely tuned to specific needs, expanding the utility of thiazolidine linker technology. An N-terminal like functionality allows access to a large series of chemoselective reactions that are already routinely carried out in protein chemistry.

Example 6

Cemadotin Derivatives with Potent Cytotoxic Activity

1. Thiol Derivatives

In the search for novel Cemadotin derivatives modified for antibody conjugation, we synthesized C-terminal thiol analogues of the original Cemadotin scaffold (FIG. 19). The analogue of cemadotin CemCH$_2$—SH was synthesized by hydrolysis of the corresponding thioester derivative assembled starting from S-4-(aminomethyl)benzyl ethanethioate (FIG. 19a) and the pentapeptide P5, which, in-turn, was produced by step-wise solid phase peptide synthesis (FIG. 19b).

Cem-CH$_2$—SH cell killing ability was evaluated by cytotoxicity assays: one non-tumor cell line (human embryonic kidney cells, HEK 293T) and two tumor cell lines, murine F9 teratocarcinoma cells (F9) and human promyelocytic leukemia cells (HL60), were incubated over 3 days with different concentrations of non-modified cemadotin and the derivative Cem-CH$_2$—SH (FIG. 20). The derivative Cem-CH$_2$—SH exhibited loss of potency depending on the cell line used, in comparison to non-modified cemadotin.

With respect to Cem-CHO, Cem-CH$_2$—SH represents a useful, but poorer cytotoxic drug (loss of up to two orders of magnitude in in-vitro cell killing ability).

The following analogues as of Cem-CH$_2$—SH are alternatives which possess modified cytotoxic activity: thiophenol derivative (Cem-SH), phenylethanethiol derivatives (Cem-CH$_2$—CH$_2$—SH), 1-phenyl ethane and 2-phenyl propyl thiol (Cem-CH(CH$_3$)SH, Cem(CH$_3$)$_2$SH), appropriate ortho and meta derivatives of the aforementioned compounds, and corresponding heterocycles. Moreover appropriately positioned electrowithdrawing as well as electrodonating substituents can also be added to the aromatic cycles in order to tune the thiol reactivity (FIG. 21)

Thiol derivatives of cemadotin in general can be coupled to non-internalizing antibody at cysteine residues (e.g. SIP, Diabody-Cys, etc) using linkerless coupling chemistry for ADC preparation. This chemistry, based on direct disulfide bond formation between non-internalizing antibody and thiol-containing drugs, allows the progressive amplification of drug release, as tumor cell lysis mediates glutathione and cysteine release to the surrounding tissue.

2. Alcohol Derivatives

In a screen for possible functional groups, suitable for coupling to antibodies, we identified esters and carbamates as potentially interesting groups for their stability properties. In order to access them, an alcohol derivative of Cemadotin is desirable.

We synthesized accordingly the phenol derivative of Cemadotin (Cem-OH, FIG. 22a), and found that it had also cell killing ability. In particular in the case of F9 tumor cells, only a factor 5 was lost with respect to cemadotin (FIG. 22b). In this case, an analogue strategy as applied to the thiol derivative can be applied in order to improve the respective cytotoxic abilities (FIG. 22c), generating the valid alternatives to Cem-OH set forth in FIG. 22c.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biochemistry and immunology or related fields are intended to be within the scope of the following claims.

The invention claimed is:

1. An antibody-drug conjugate comprising a protein attached by a linker to one or more drugs, wherein the linker comprises a heterocyclic 1,3-substituted five- or six-member ring, having the following structure:

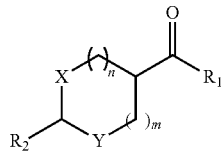

wherein X and Y are, each independently, selected from the group consisting of sulphur, nitrogen and oxygen
wherein n, m independently vary between 0 and 1, provided that n and m are not both 0;
and wherein R1 and/or R2 are selected from the group consisting of a drug or an antibody molecule to which the linker is attached,
and wherein the linker has a half-life of from about 1 hour to about 50 hours in phosphate buffered saline at 37° C.

2. The antibody-drug conjugate according to claim 1, wherein the linker is selected from the group consisting of thiazolidine, 1,3-thiazinane, oxazolidine, 1,3-dioxolane, 1,3-dithiolane, 1,3-dithiane, 1,3-oxathiolane, 1,3-oxathiane, imidazolidine, and hexahydropyrimidine.

3. The antibody-drug conjugate according to claim 2, wherein the linker is thiazolidine.

4. The antibody-drug conjugate of claim 1, wherein the linker is attached at an N-terminal cysteine of the protein.

5. The antibody-drug conjugate according to claim 1, wherein the cytotoxic drug is dolastatin.

6. The antibody-drug conjugate according to claim 5, wherein said dolastatin is dolastatin-15.

7. The antibody-drug conjugate according to claim 1, wherein the antibody is a monoclonal antibody.

8. The antibody-drug conjugate of claim 7 wherein the monoclonal antibody is a human monoclonal antibody selected from the group consisting of F8, L19 or F16.

9. A pharmaceutical composition comprising the conjugate of claim 1 or a pharmaceutically acceptable salt thereof, and a pharmaceutically acceptable diluent, carrier or excipient.

10. The antibody-drug conjugate of claim 1, having the following structure:

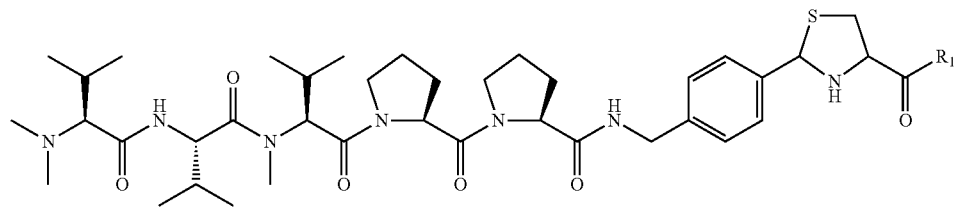

wherein R1 is the antibody molecule to which the linker is attached.

* * * * *

SEQUENCE LISTING

<160> NUMBER OF SEQ ID NOS: 12

<210> SEQ ID NO 1
<211> LENGTH: 790
<212> TYPE: DNA
<213> ORGANISM: artificial sequence
<220> FEATURE:
<223> OTHER INFORMATION: HindIII - Leader Sequence - Cys - VH (F8) - 5aa
      (linker) - VL (F8) - STOPSTOP - NotI

<400> SEQUENCE: 1
cccaagcttg tcgaccatgg gctggagcct gatcctcctg ttcctcgtcg ctgtggctac      60
aggtgtgcac tcgtgcgagg tgcagctgtt ggagtctggg ggaggcttgg tacagcctgg     120
ggggtccctg agactctcct gtgcagcctc tggattcacc tttagcctgt ttacgatgag     180
ctgggtccgc caggctccag gaagggggct ggagtgggtc tcagctatta gtggtagtgg     240
tggtagcaca tactacgcag actccgtgaa gggccggttc accatctcca gagacaattc     300
caagaacacg ctgtatctgc aaatgaacag cctgagagcc gaggacacgg ccgtatatta     360
ctgtgcgaaa agtactcatt tgtatctttt tgactactgg ggccagggaa ccctggtcac     420
cgtctcgagt ggcggtagcg aggggaaat tgtgttgacg cagtctccag gcaccctgtc     480
tttgtctcca ggggaaagag ccaccctctc ctgcagggcc agtcagagtg ttagcatgcc     540 gttttttagcc tggtaccagc agaaacctgg ccaggctccc aggctcctca tctatggtgc     600
atccagcagg gccactggca tcccagacag gttcagtggc agtgggtctg gacagactt     660 cactctcacc atcagcagac tggagcctga agattttgca gtgtattact gtcagcagat     720
gcgtggtcgg ccgccgacgt tcggccaagg gaccaaggtg gaaatcaaat aagcggccgc     780
aaaaggaaaa                                                            790

<210> SEQ ID NO 2
<211> LENGTH: 251
<212> TYPE: PRT
<213> ORGANISM: artificial sequence
<220> FEATURE:
<223> OTHER INFORMATION: HindIII - Leader Sequence - Cys - VH (F8) - 5aa
      (linker) - VL (F8) - STOPSTOP - NotI

<400> SEQUENCE: 2

Met Gly Trp Ser Leu Ile Leu Leu Phe Leu Val Ala Val Ala Thr Gly
1               5                   10                  15

Val His Ser Cys Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Leu Phe Thr Met Ser Trp Val Arg Gln Ala Pro Gly Lys Gly
    50                  55                  60

Leu Glu Trp Val Ser Ala Ile Ser Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Ser Thr His Leu Tyr Leu Phe Asp Tyr Trp
        115                 120                 125

Gly Gln Gly Thr Leu Val Thr Val Ser Ser Gly Gly Ser Gly Gly Glu
    130                 135                 140

```
Ile Val Leu Thr Gln Ser Pro Gly Thr Leu Ser Leu Ser Pro Gly Glu
145                 150                 155                 160

Arg Ala Thr Leu Ser Cys Arg Ala Ser Gln Ser Val Ser Met Pro Phe
                165                 170                 175

Leu Ala Trp Tyr Gln Gln Lys Pro Gly Gln Ala Pro Arg Leu Leu Ile
            180                 185                 190

Tyr Gly Ala Ser Ser Arg Ala Thr Gly Ile Pro Asp Arg Phe Ser Gly
        195                 200                 205

Ser Gly Ser Gly Thr Asp Phe Thr Leu Thr Ile Ser Arg Leu Glu Pro
    210                 215                 220

Glu Asp Phe Ala Val Tyr Tyr Cys Gln Gln Met Arg Gly Arg Pro Pro
225                 230                 235                 240

Thr Phe Gly Gln Gly Thr Lys Val Glu Ile Lys
                245                 250
```

<210> SEQ ID NO 3
<211> LENGTH: 26
<212> TYPE: DNA
<213> ORGANISM: artificial sequence
<220> FEATURE:
<223> OTHER INFORMATION: primer

<400> SEQUENCE: 3
tgcgaggtgc agctgttgga gtctgg                                  26

<210> SEQ ID NO 4
<211> LENGTH: 55
<212> TYPE: DNA
<213> ORGANISM: artificial sequence
<220> FEATURE:
<223> OTHER INFORMATION: primer

<400> SEQUENCE: 4
gttcctcgtc gctgtggcta caggtgtgca ctcgtgcgag gtgcagctgt tggag   55

<210> SEQ ID NO 5
<211> LENGTH: 57
<212> TYPE: DNA
<213> ORGANISM: artificial sequence
<220> FEATURE:
<223> OTHER INFORMATION: primer

<400> SEQUENCE: 5
cccaagcttg tcgaccatgg gctggagcct gatcctcctg ttcctcgtcg ctgtggc   57

<210> SEQ ID NO 6
<211> LENGTH: 42
<212> TYPE: DNA
<213> ORGANISM: artificial sequence
<220> FEATURE:
<223> OTHER INFORMATION: primer

<400> SEQUENCE: 6
ttttcctttt gcggccgctt atttgatttc caccttggtc cc                42

<210> SEQ ID NO 7
<211> LENGTH: 793
<212> TYPE: DNA
<213> ORGANISM: artificial sequence
<220> FEATURE:
<223> OTHER INFORMATION: HindIII - Leader Sequence - Cys - Gly - VH
      (F8) - 5aa (linker) - VL (F8) - STOPSTOP - NotI

<400> SEQUENCE: 7

-continued

```
cccaagcttg tcgaccatgg gctggagcct gatcctcctg ttcctcgtcg ctgtggctac      60
aggtgtgcac tcgtgcggtg aggtgcagct gttggagtct ggggggaggct tggtacagcc    120
tgggggtcc ctgagactct cctgtgcagc ctctggattc acctttagcc tgtttacgat     180
gagctgggtc cgccaggctc agggaaggg gctgagtgg gtctcagcta ttagtggtag      240
tggtggtagc acatactacg cagactccgt gaagggccgg ttcaccatct ccagagacaa    300
ttccaagaac acgctgtatc tgcaaatgaa cagcctgaga gccgaggaca cggccgtata    360
ttactgtgcg aaaagtactc atttgtatct ttttgactac tggggccagg gaaccctggt    420
caccgtctcg agtggcggta gcggagggga aattgtgttg acgcagtctc caggcaccct    480
gtctttgtct ccaggggaaa gagccaccct ctcctgcagg gccagtcaga gtgttagcat    540
gccgttttta gcctggtacc agcagaaacc tggccaggct cccaggctcc tcatctatgg    600
tgcatccagc agggccactg gcatcccaga caggttcagt ggcagtgggt ctgggacaga    660
cttcactctc accatcagca gactggagcc tgaagatttt gcagtgtatt actgtcagca    720
gatgcgtggt cggccgccga cgttcggcca agggaccaag gtggaaatca ataagcggc    780
cgcaaaagga aaa                                                       793
```

<210> SEQ ID NO 8
<211> LENGTH: 252
<212> TYPE: PRT
<213> ORGANISM: artificial sequence
<220> FEATURE:
<223> OTHER INFORMATION: HindIII - Leader Sequence - Cys - Gly - VH
      (F8) - 5aa (linker) - VL (F8) - STOPSTOP - NotI

<400> SEQUENCE: 8

```
Met Gly Trp Ser Leu Ile Leu Leu Phe Leu Val Ala Val Ala Thr Gly
1               5                   10                  15

Val His Ser Cys Gly Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Leu Phe Thr Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Ser Thr His Leu Tyr Leu Phe Asp Tyr
        115                 120                 125

Trp Gly Gln Gly Thr Leu Val Thr Val Ser Ser Gly Gly Ser Gly Gly
    130                 135                 140

Glu Ile Val Leu Thr Gln Ser Pro Gly Thr Leu Ser Leu Ser Pro Gly
145                 150                 155                 160

Glu Arg Ala Thr Leu Ser Cys Arg Ala Ser Gln Ser Val Ser Met Pro
                165                 170                 175

Phe Leu Ala Trp Tyr Gln Gln Lys Pro Gly Gln Ala Pro Arg Leu Leu
            180                 185                 190

Ile Tyr Gly Ala Ser Ser Arg Ala Thr Gly Ile Pro Asp Arg Phe Ser
        195                 200                 205
```

```
Gly Ser Gly Ser Gly Thr Asp Phe Thr Leu Thr Ile Ser Arg Leu Glu
        210                 215                 220

Pro Glu Asp Phe Ala Val Tyr Tyr Cys Gln Gln Met Arg Gly Arg Pro
225                 230                 235                 240

Pro Thr Phe Gly Gln Gly Thr Lys Val Glu Ile Lys
                245                 250

<210> SEQ ID NO 9
<211> LENGTH: 29
<212> TYPE: DNA
<213> ORGANISM: artificial sequence
<220> FEATURE:
<223> OTHER INFORMATION: primer

<400> SEQUENCE: 9
tgcggtgagg tgcagctgtt ggagtctgg                                         29

<210> SEQ ID NO 10
<211> LENGTH: 52
<212> TYPE: DNA
<213> ORGANISM: artificial sequence
<220> FEATURE:
<223> OTHER INFORMATION: primer

<400> SEQUENCE: 10
gttcctcgtc gctgtggcta caggtgtgca ctcgtgcggt gaggtgcagc tg               52

<210> SEQ ID NO 11
<211> LENGTH: 57
<212> TYPE: DNA
<213> ORGANISM: artificial sequence
<220> FEATURE:
<223> OTHER INFORMATION: primer

<400> SEQUENCE: 11
cccaagcttg tcgaccatgg gctggagcct gatcctcctg ttcctcgtcg ctgtggc          57

<210> SEQ ID NO 12
<211> LENGTH: 42
<212> TYPE: DNA
<213> ORGANISM: artificial sequence
<220> FEATURE:
<223> OTHER INFORMATION: primer

<400> SEQUENCE: 12
ttttcctttt gcggccgctt atttgatttc caccttggtc cc                          42
```